United States Patent
Kilgard et al.

(10) Patent No.: US 8,489,185 B2
(45) Date of Patent: Jul. 16, 2013

(54) TIMING CONTROL FOR PAIRED PLASTICITY

(75) Inventors: Michael Kilgard, Dallas, TX (US); Larry Cauller, Plano, TX (US); Navzer Engineer, Plano, TX (US); Christa McIntyre, Richardson, TX (US); Will Rosellini, Dallas, TX (US)

(73) Assignee: The Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 12/485,857

(22) Filed: Jun. 16, 2009

(65) Prior Publication Data

US 2010/0004717 A1    Jan. 7, 2010

Related U.S. Application Data

(63) Continuation of application No. 12/845,040, filed on Jun. 15, 2009.

(60) Provisional application No. 61/077,648, filed on Jul. 2, 2008, provisional application No. 61/078,954, filed on Jul. 8, 2008, provisional application No. 61/086,116, filed on Aug. 4, 2008, provisional application No. 61/149,387, filed on Feb. 3, 2009.

(51) Int. Cl.
*A61N 1/00*    (2006.01)

(52) U.S. Cl.
USPC ............ 607/2; 607/1; 607/3; 607/44; 607/45; 607/48; 607/49

(58) Field of Classification Search
USPC .................................................. 607/1–3, 45
See application file for complete search history.

(56) References Cited

U.S. PATENT DOCUMENTS

| | | | |
|---|---|---|---|
| 2,641,259 A | 6/1953 | Bartrow | |
| 3,750,653 A | 8/1973 | Simon | |
| 3,796,221 A | 3/1974 | Hagfors | |

(Continued)

FOREIGN PATENT DOCUMENTS

| | | |
|---|---|---|
| CN | 101648053 A | 2/2010 |
| DE | 3405630 C1 | 6/1985 |

(Continued)

OTHER PUBLICATIONS

Kipke, D., Vetter, R., Williams, J., and Hetke, J., "Silicon-Substrate Intracortical Microelectrode Arrays for Long-Term Recording of Neuronal Spike Activity in Cerebral Cortex", IEEE Transactions on Neural Systems and Rehabilitation Engineering, vol. 11, No. 2, Jun. 2003, pp. 151-155.

(Continued)

*Primary Examiner* — Niketa Patel
*Assistant Examiner* — Mallika D Fairchild
(74) *Attorney, Agent, or Firm* — Lowe Hauptman Ham & Berner, LLP

(57) ABSTRACT

Systems, methods and devices for paired training include timing controls so that training and neural stimulation can be provided simultaneously. Paired trainings may include therapies, rehabilitation and performance enhancement training. Stimulations of nerves such as the vagus nerve that affect subcortical regions such as the nucleus basalis, locus coeruleus or amygdala induce plasticity in the brain, enhancing the effects of a variety of therapies, such as those used to treat tinnitus, stroke, traumatic brain injury and post-traumatic stress disorder.

18 Claims, 9 Drawing Sheets

U.S. PATENT DOCUMENTS

| | | |
|---|---|---|
| 3,830,242 A | 8/1974 | Greatbatch |
| 3,885,211 A | 5/1975 | Gutai |
| 3,893,462 A | 7/1975 | Manning |
| 3,942,535 A | 3/1976 | Schulman |
| 4,019,519 A | 4/1977 | Geerling |
| 4,044,775 A | 8/1977 | McNichols |
| 4,154,239 A | 5/1979 | Turley |
| 4,167,179 A | 9/1979 | Kirsch |
| 4,361,153 A | 11/1982 | Slocum et al. |
| 4,399,818 A | 8/1983 | Money |
| 4,541,432 A | 9/1985 | Molina-Negro et al. |
| 4,592,359 A | 6/1986 | Galbraith |
| 4,612,934 A | 9/1986 | Borkan |
| 4,661,103 A | 4/1987 | Harman |
| 4,723,536 A | 2/1988 | Rauscher et al. |
| 4,750,499 A | 6/1988 | Hoffer |
| 4,832,033 A | 5/1989 | Maher et al. |
| 4,883,067 A | 11/1989 | Knispel et al. |
| 4,902,987 A | 2/1990 | Albright |
| 4,932,405 A | 6/1990 | Peeters et al. |
| 4,977,895 A | 12/1990 | Tannenbaum |
| 5,192,285 A | 3/1993 | Bolscher |
| 5,193,539 A | 3/1993 | Schulman et al. |
| 5,193,540 A | 3/1993 | Schulman et al. |
| 5,222,494 A | 6/1993 | Baker, Jr. |
| 5,234,316 A | 8/1993 | Rupprecht |
| 5,250,026 A | 10/1993 | Ehrlich et al. |
| 5,265,624 A | 11/1993 | Bowman |
| 5,279,554 A | 1/1994 | Turley |
| 5,288,291 A | 2/1994 | Teoh |
| 5,312,439 A | 5/1994 | Loeb |
| 5,324,316 A | 6/1994 | Schulman et al. |
| 5,330,515 A | 7/1994 | Rutecki et al. |
| 5,335,657 A | 8/1994 | Terry, Jr. et al. |
| 5,363,858 A | 11/1994 | Farwell |
| 5,405,367 A | 4/1995 | Schulman et al. |
| 5,474,082 A | 12/1995 | Junker |
| 5,559,507 A | 9/1996 | Beigel |
| 5,571,148 A | 11/1996 | Loeb et al. |
| 5,593,432 A | 1/1997 | Crowther et al. |
| 5,662,689 A | 9/1997 | Elsberry et al. |
| 5,735,887 A | 4/1998 | Barreras, Sr. et al. |
| 5,741,316 A | 4/1998 | Chen et al. |
| 5,755,747 A | 5/1998 | Daly et al. |
| 5,776,170 A | 7/1998 | MacDonald et al. |
| 5,779,665 A | 7/1998 | Mastrototaro et al. |
| 5,782,874 A | 7/1998 | Loos |
| 5,785,680 A | 7/1998 | Niezink et al. |
| 5,800,458 A | 9/1998 | Wingrove |
| 5,814,092 A | 9/1998 | King |
| 5,833,603 A | 11/1998 | Kovacs et al. |
| 5,833,714 A | 11/1998 | Loeb |
| 5,871,512 A | 2/1999 | Hemming et al. |
| 5,899,922 A | 5/1999 | Loos |
| 5,913,882 A | 6/1999 | King |
| 5,938,690 A | 8/1999 | Law et al. |
| 5,945,938 A | 8/1999 | Chia et al. |
| 5,954,758 A | 9/1999 | Peckham et al. |
| 5,957,958 A | 9/1999 | Schulman et al. |
| 5,970,398 A | 10/1999 | Tuttle |
| 6,009,350 A | 12/1999 | Renken |
| 6,051,017 A | 4/2000 | Loeb et al. |
| 6,141,588 A | 10/2000 | Cox et al. |
| 6,164,284 A | 12/2000 | Schulman et al. |
| 6,175,764 B1 | 1/2001 | Loeb et al. |
| 6,181,965 B1 | 1/2001 | Loeb et al. |
| 6,181,969 B1 | 1/2001 | Gord |
| 6,185,452 B1 | 2/2001 | Schulman et al. |
| 6,185,455 B1 | 2/2001 | Loeb et al. |
| 6,201,980 B1 | 3/2001 | Darrow et al. |
| 6,208,894 B1 | 3/2001 | Schulman et al. |
| 6,208,902 B1 | 3/2001 | Boveja |
| 6,214,032 B1 | 4/2001 | Loeb et al. |
| 6,221,908 B1 | 4/2001 | Kilgard et al. |
| 6,240,316 B1 | 5/2001 | Richmond et al. |
| 6,263,247 B1 | 7/2001 | Mueller et al. |
| 6,270,472 B1 | 8/2001 | Antaki et al. |
| 6,308,102 B1 | 10/2001 | Sieracki et al. |
| 6,339,725 B1 * | 1/2002 | Naritoku et al. ............. 607/45 |
| 6,345,202 B2 | 2/2002 | Richmond et al. |
| 6,354,989 B1 | 3/2002 | Nudeshima |
| 6,366,814 B1 | 4/2002 | Boveja et al. |
| 6,394,947 B1 | 5/2002 | Leysieffer |
| 6,409,655 B1 | 6/2002 | Wilson et al. |
| 6,415,184 B1 | 7/2002 | Ishikawa et al. |
| 6,430,443 B1 | 8/2002 | Karell |
| 6,430,444 B1 | 8/2002 | Borza |
| 6,447,448 B1 | 9/2002 | Ishikawa et al. |
| 6,456,866 B1 | 9/2002 | Tyler et al. |
| 6,458,157 B1 | 10/2002 | Suaning |
| 6,463,328 B1 | 10/2002 | John |
| 6,480,730 B2 | 11/2002 | Darrow et al. |
| 6,505,075 B1 | 1/2003 | Weiner |
| 6,516,808 B2 | 2/2003 | Schulman |
| 6,546,290 B1 | 4/2003 | Shloznikov |
| 6,567,689 B2 | 5/2003 | Burbank et al. |
| 6,572,543 B1 | 6/2003 | Christopherson et al. |
| 6,582,441 B1 | 6/2003 | He et al. |
| 6,585,644 B2 | 7/2003 | Lebel et al. |
| 6,591,139 B2 | 7/2003 | Loftin et al. |
| 6,592,518 B2 | 7/2003 | Denker et al. |
| 6,626,676 B2 | 9/2003 | Freer |
| 6,650,943 B1 | 11/2003 | Whitehurst et al. |
| 6,658,297 B2 | 12/2003 | Loeb |
| 6,658,301 B2 | 12/2003 | Loeb et al. |
| 6,676,675 B2 | 1/2004 | Mallapragada et al. |
| 6,690,974 B2 | 2/2004 | Archer et al. |
| 6,695,885 B2 | 2/2004 | Schulman et al. |
| 6,712,753 B2 | 3/2004 | Manne |
| 6,721,603 B2 | 4/2004 | Zabara et al. |
| 6,731,979 B2 | 5/2004 | MacDonald |
| 6,733,485 B1 | 5/2004 | Whitehurst et al. |
| 6,735,474 B1 | 5/2004 | Loeb et al. |
| 6,735,475 B1 | 5/2004 | Whitehurst et al. |
| 6,760,626 B1 | 7/2004 | Boveja |
| 6,788,975 B1 | 9/2004 | Whitehurst et al. |
| 6,796,935 B1 | 9/2004 | Savino |
| 6,804,561 B2 | 10/2004 | Stover |
| 6,829,508 B2 | 12/2004 | Schulman et al. |
| 6,832,114 B1 | 12/2004 | Whitehurst et al. |
| 6,836,685 B1 | 12/2004 | Fitz |
| 6,844,023 B2 | 1/2005 | Schulman et al. |
| 6,845,267 B2 | 1/2005 | Harrison et al. |
| 6,855,115 B2 | 2/2005 | Fonseca et al. |
| 6,871,099 B1 | 3/2005 | Whitehurst et al. |
| 6,885,888 B2 | 4/2005 | Rezai |
| 6,895,279 B2 | 5/2005 | Loeb et al. |
| 6,895,280 B2 | 5/2005 | Meadows et al. |
| 6,941,171 B2 | 9/2005 | Mann et al. |
| 6,971,984 B2 | 12/2005 | Ardizzone |
| 6,974,437 B2 | 12/2005 | Lebel et al. |
| 6,990,377 B2 * | 1/2006 | Gliner et al. ............. 607/54 |
| 7,003,352 B1 | 2/2006 | Whitehurst |
| 7,006,870 B1 | 2/2006 | Whitehurst et al. |
| 7,006,875 B1 | 2/2006 | Kuzma et al. |
| 7,013,177 B1 | 3/2006 | Whitehurst et al. |
| 7,024,247 B2 | 4/2006 | Gliner et al. |
| 7,027,860 B2 | 4/2006 | Bruninga et al. |
| 7,054,689 B1 | 5/2006 | Whitehurst et al. |
| 7,054,691 B1 | 5/2006 | Kuzma et al. |
| 7,062,330 B1 | 6/2006 | Boveja et al. |
| 7,076,307 B2 | 7/2006 | Boveja et al. |
| 7,103,408 B2 | 9/2006 | Haller et al. |
| 7,107,103 B2 | 9/2006 | Schulman et al. |
| 7,114,502 B2 | 10/2006 | Schulman et al. |
| 7,117,034 B2 | 10/2006 | Kronberg |
| 7,132,173 B2 | 11/2006 | Daulton |
| 7,146,217 B2 | 12/2006 | Firlik et al. |
| 7,147,604 B1 | 12/2006 | Allen et al. |
| 7,149,574 B2 | 12/2006 | Yun et al. |
| 7,155,279 B2 | 12/2006 | Whitehurst et al. |
| 7,174,215 B2 | 2/2007 | Bradley |
| 7,184,837 B2 | 2/2007 | Goetz |
| 7,187,968 B2 | 3/2007 | Wolf et al. |
| 7,191,012 B2 | 3/2007 | Boveja et al. |
| 7,194,007 B1 | 3/2007 | Beadle et al. |
| 7,209,787 B2 | 4/2007 | DiLorenzo |

| Patent No. | Date | Inventor |
|---|---|---|
| 7,209,788 B2 | 4/2007 | Nicolelis et al. |
| 7,209,792 B1 | 4/2007 | Parramon et al. |
| 7,211,048 B1 | 5/2007 | Najafi et al. |
| 7,212,110 B1 | 5/2007 | Martin et al. |
| 7,212,866 B1 | 5/2007 | Griffith |
| 7,221,981 B2 | 5/2007 | Gliner |
| 7,231,256 B2 | 6/2007 | Wahlstrand et al. |
| 7,236,822 B2 | 6/2007 | Dobak, III |
| 7,236,830 B2 | 6/2007 | Gliner |
| 7,236,831 B2 | 6/2007 | Firlik et al. |
| 7,256,695 B2 | 8/2007 | Hamel et al. |
| 7,290,890 B2 | 11/2007 | Yoshida et al. |
| 7,292,890 B2 | 11/2007 | Whitehurst et al. |
| 7,299,096 B2 | 11/2007 | Balzer et al. |
| 7,302,298 B2 | 11/2007 | Lowry et al. |
| 7,305,268 B2 | 12/2007 | Gliner et al. |
| 7,324,852 B2 | 1/2008 | Barolat et al. |
| 7,328,069 B2 | 2/2008 | Gerber |
| 7,330,756 B2 | 2/2008 | Marnfeldt |
| 7,337,004 B2 | 2/2008 | Classen et al. |
| 7,353,064 B2 | 4/2008 | Gliner et al. |
| 7,359,751 B1 | 4/2008 | Erickson et al. |
| 7,361,135 B2 | 4/2008 | Drobnik et al. |
| 7,369,897 B2 | 5/2008 | Boveja et al. |
| 7,373,204 B2 | 5/2008 | Gelfand et al. |
| 7,384,403 B2 | 6/2008 | Sherman |
| 7,386,348 B2 | 6/2008 | North et al. |
| 7,389,145 B2 | 6/2008 | Kilgore et al. |
| 7,406,105 B2 | 7/2008 | DelMain et al. |
| 7,437,195 B2 | 10/2008 | Policker et al. |
| 7,437,196 B2 | 10/2008 | Wyler et al. |
| 7,463,927 B1 | 12/2008 | Chaouat |
| 7,481,771 B2 | 1/2009 | Fonseca et al. |
| 7,483,747 B2 | 1/2009 | Gliner et al. |
| 7,489,561 B2 | 2/2009 | Armstrong et al. |
| 7,489,966 B2 | 2/2009 | Leinders et al. |
| 7,493,172 B2 | 2/2009 | Whitehurst et al. |
| 7,526,341 B2 | 4/2009 | Goetz et al. |
| 7,529,582 B1 | 5/2009 | DiLorenzo |
| 7,542,804 B2 | 6/2009 | Mandell |
| 7,547,353 B2 | 6/2009 | Reyes et al. |
| 7,555,344 B2 | 6/2009 | Maschino et al. |
| 7,555,345 B2 | 6/2009 | Wahlstrand et al. |
| 7,555,347 B2 | 6/2009 | Loeb |
| 7,558,631 B2 | 7/2009 | Cowan et al. |
| 7,563,279 B2 | 7/2009 | Lasater |
| 7,565,199 B2 | 7/2009 | Sheffield et al. |
| 7,565,200 B2 | 7/2009 | Wyler et al. |
| 7,577,481 B2 | 8/2009 | Firlik et al. |
| 7,590,454 B2 | 9/2009 | Garabedian et al. |
| 7,593,776 B2 | 9/2009 | Loeb et al. |
| 7,596,413 B2 | 9/2009 | Libbus et al. |
| 7,603,174 B2 | 10/2009 | De Ridder |
| 7,603,178 B2 | 10/2009 | North et al. |
| 7,613,519 B2 | 11/2009 | DeRidder |
| 7,613,520 B2 | 11/2009 | De Ridder |
| 7,616,990 B2 | 11/2009 | Chavan et al. |
| 7,630,771 B2 | 12/2009 | Cauller |
| 7,634,317 B2 | 12/2009 | Ben-David et al. |
| 7,636,603 B1 | 12/2009 | Overstreet et al. |
| 7,715,915 B1 | 5/2010 | Ryu et al. |
| 7,765,013 B2 | 7/2010 | Blick et al. |
| 7,769,466 B2 | 8/2010 | Denker et al. |
| 7,786,867 B2 | 8/2010 | Hamel et al. |
| 7,801,615 B2 | 9/2010 | Meadows et al. |
| 7,822,480 B2 | 10/2010 | Park et al. |
| 2001/0016683 A1 | 8/2001 | Darrow et al. |
| 2002/0022872 A1 | 2/2002 | Gielen et al. |
| 2002/0029005 A1 | 3/2002 | Levendowski et al. |
| 2002/0051806 A1 | 5/2002 | Mallapragada et al. |
| 2002/0058853 A1 | 5/2002 | Kaplan |
| 2002/0077672 A1 | 6/2002 | Govari et al. |
| 2002/0193845 A1 | 12/2002 | Greenberg et al. |
| 2003/0004411 A1 | 1/2003 | Govari et al. |
| 2003/0013948 A1 | 1/2003 | Russell |
| 2003/0014091 A1 | 1/2003 | Rastegar et al. |
| 2003/0114899 A1 | 6/2003 | Woods et al. |
| 2003/0139677 A1 | 7/2003 | Fonseca et al. |
| 2003/0139783 A1 | 7/2003 | Kilgore et al. |
| 2003/0144709 A1 | 7/2003 | Zabara et al. |
| 2003/0171758 A1 | 9/2003 | Gibson et al. |
| 2003/0225331 A1 | 12/2003 | Diederich et al. |
| 2004/0031065 A1 | 2/2004 | Barth |
| 2004/0172075 A1 | 9/2004 | Shafer et al. |
| 2004/0172083 A1 | 9/2004 | Penner |
| 2004/0176831 A1 | 9/2004 | Gliner et al. |
| 2004/0181261 A1 | 9/2004 | Manne |
| 2004/0253209 A1 | 12/2004 | Soykan et al. |
| 2004/0267152 A1 | 12/2004 | Pineda |
| 2005/0015014 A1 | 1/2005 | Fonseca et al. |
| 2005/0021100 A1 | 1/2005 | Tsukamoto et al. |
| 2005/0070974 A1 | 3/2005 | Knudson et al. |
| 2005/0131386 A1 | 6/2005 | Freeman et al. |
| 2005/0137652 A1 | 6/2005 | Cauller et al. |
| 2005/0143789 A1 | 6/2005 | Whitehurst et al. |
| 2005/0209667 A1 | 9/2005 | Erickson et al. |
| 2005/0222641 A1 | 10/2005 | Pless |
| 2005/0245989 A1 | 11/2005 | Davis |
| 2005/0256551 A1 | 11/2005 | Schulman et al. |
| 2005/0258242 A1 | 11/2005 | Zarembo |
| 2006/0058570 A1 | 3/2006 | Rapach et al. |
| 2006/0173263 A1 | 8/2006 | He et al. |
| 2006/0173493 A1 | 8/2006 | Armstrong et al. |
| 2006/0195154 A1 | 8/2006 | Jaax et al. |
| 2006/0206149 A1 | 9/2006 | Yun |
| 2006/0224214 A1 | 10/2006 | Koller et al. |
| 2006/0241354 A1 | 10/2006 | Allen |
| 2006/0247719 A1 | 11/2006 | Maschino et al. |
| 2006/0271110 A1 | 11/2006 | Vernon et al. |
| 2007/0010809 A1 | 1/2007 | Hovda et al. |
| 2007/0021786 A1 | 1/2007 | Parnis et al. |
| 2007/0027486 A1 | 2/2007 | Armstrong |
| 2007/0027504 A1* | 2/2007 | Barrett et al. .................. 607/55 |
| 2007/0032734 A1 | 2/2007 | Najafi et al. |
| 2007/0077265 A1 | 4/2007 | Klueh et al. |
| 2007/0123938 A1 | 5/2007 | Haller et al. |
| 2007/0179534 A1 | 8/2007 | Firlik et al. |
| 2007/0191908 A1 | 8/2007 | Jacob et al. |
| 2007/0225767 A1 | 9/2007 | Daly et al. |
| 2007/0265172 A1 | 11/2007 | Patel et al. |
| 2007/0265683 A1 | 11/2007 | Ehrlich |
| 2007/0275035 A1 | 11/2007 | Herman et al. |
| 2007/0293908 A1 | 12/2007 | Cowan et al. |
| 2008/0033351 A1 | 2/2008 | Trogden et al. |
| 2008/0033502 A1 | 2/2008 | Harris et al. |
| 2008/0058892 A1 | 3/2008 | Haefner et al. |
| 2008/0065182 A1 | 3/2008 | Strother et al. |
| 2008/0084898 A1 | 4/2008 | Miyaho et al. |
| 2008/0084911 A1 | 4/2008 | Yerlikaya |
| 2008/0084941 A1 | 4/2008 | Mohanty et al. |
| 2008/0084951 A1 | 4/2008 | Chen et al. |
| 2008/0084972 A1 | 4/2008 | Burke et al. |
| 2008/0084986 A1 | 4/2008 | Kumarasamy et al. |
| 2008/0103548 A1 | 5/2008 | Fowler et al. |
| 2008/0109046 A1 | 5/2008 | Lima et al. |
| 2008/0243204 A1 | 10/2008 | Uthman et al. |
| 2008/0259681 A1 | 10/2008 | Branch et al. |
| 2008/0275369 A1 | 11/2008 | Fandriks |
| 2008/0281210 A1 | 11/2008 | Nunez et al. |
| 2008/0281212 A1 | 11/2008 | Nunez et al. |
| 2008/0281368 A1 | 11/2008 | Bulkes et al. |
| 2008/0319506 A1 | 12/2008 | Cauller |
| 2009/0015331 A1 | 1/2009 | Segarra |
| 2009/0024042 A1 | 1/2009 | Nunez et al. |
| 2009/0024189 A1 | 1/2009 | Lee et al. |
| 2009/0030476 A1 | 1/2009 | Hargrove |
| 2009/0049321 A1 | 2/2009 | Balatsos et al. |
| 2009/0132003 A1 | 5/2009 | Borgens et al. |
| 2009/0149918 A1 | 6/2009 | Krulevitch et al. |
| 2009/0157142 A1 | 6/2009 | Cauller |
| 2009/0157145 A1 | 6/2009 | Cauller |
| 2009/0157147 A1 | 6/2009 | Cauller et al. |
| 2009/0157150 A1 | 6/2009 | Cauller |
| 2009/0157151 A1 | 6/2009 | Cauller et al. |
| 2009/0163889 A1 | 6/2009 | Cauller et al. |
| 2009/0198293 A1 | 8/2009 | Cauller et al. |
| 2009/0209804 A1 | 8/2009 | Seiler et al. |
| 2009/0216115 A1 | 8/2009 | Seiler et al. |

| | | | |
|---|---|---|---|
| 2009/0247939 | A1 | 10/2009 | Rue et al. |
| 2009/0264813 | A1 | 10/2009 | Chang |
| 2009/0292325 | A1 | 11/2009 | Cederna et al. |
| 2009/0312594 | A1 | 12/2009 | Lamoureux et al. |
| 2010/0003656 | A1 | 1/2010 | Kilgard et al. |
| 2010/0004705 | A1 | 1/2010 | Kilgard et al. |
| 2010/0022908 | A1 | 1/2010 | Cauller |
| 2010/0036211 | A1 | 2/2010 | La Rue et al. |
| 2010/0036445 | A1 | 2/2010 | Sakai et al. |
| 2010/0057160 | A1 | 3/2010 | De Ridder |
| 2010/0063564 | A1 | 3/2010 | Libbus et al. |
| 2010/0069992 | A1 | 3/2010 | Aghassian et al. |
| 2010/0069994 | A1 | 3/2010 | Cauller |
| 2010/0100010 | A1 | 4/2010 | Andarawis et al. |
| 2010/0100079 | A1 | 4/2010 | Berkcan et al. |
| 2010/0106217 | A1 | 4/2010 | Colborn |
| 2010/0125314 | A1 | 5/2010 | Bradley et al. |
| 2010/0137961 | A1 | 6/2010 | Moffitt et al. |
| 2010/0145216 | A1 | 6/2010 | He et al. |
| 2010/0145401 | A1 | 6/2010 | Pastore et al. |
| 2010/0174341 | A1 | 7/2010 | Bolea et al. |
| 2010/0222844 | A1 | 9/2010 | Troosters et al. |
| 2010/0331921 | A1 | 12/2010 | Bornzin et al. |
| 2011/0004266 | A1 | 1/2011 | Sharma |

FOREIGN PATENT DOCUMENTS

| | | |
|---|---|---|
| DE | 2004050616 B3 | 3/2006 |
| DE | 112008001669 T5 | 5/2010 |
| DE | 11208003192 T5 | 10/2010 |
| DE | 11208003194 T5 | 2/2011 |
| DE | 11208003180 T5 | 3/2011 |
| EP | 0247649 A1 | 2/1987 |
| EP | 1575665 A1 | 9/2005 |
| EP | 1719540 A3 | 8/2006 |
| EP | 1785160 A2 | 5/2007 |
| WO | 96/19257 A1 | 6/1996 |
| WO | 98/17628 A2 | 4/1998 |
| WO | 98/43701 A1 | 10/1998 |
| WO | 02/082982 A1 | 10/2002 |
| WO | 03/003791 A1 | 1/2003 |
| WO | 03/015863 A2 | 2/2003 |
| WO | 03/018113 A1 | 3/2003 |
| WO | 03/076010 A1 | 9/2003 |
| WO | 2004060144 A2 | 7/2004 |
| WO | 2005061045 A1 | 7/2005 |
| WO | 2005067792 A1 | 7/2005 |
| WO | 2006020377 A2 | 2/2006 |
| WO | 2006029007 A2 | 3/2006 |
| WO | 2006029257 A2 | 3/2006 |
| WO | 2006091611 A1 | 8/2006 |
| WO | 2007073557 A2 | 6/2007 |
| WO | 2007098202 A3 | 8/2007 |
| WO | 2007106692 A2 | 9/2007 |
| WO | 2007136657 A2 | 11/2007 |
| WO | 2007146213 A2 | 12/2007 |
| WO | 2008103977 A2 | 8/2008 |
| WO | 2008133797 A1 | 11/2008 |
| WO | 2008150348 A1 | 12/2008 |
| WO | 2008151059 A2 | 12/2008 |
| WO | 2009018172 A2 | 2/2009 |
| WO | 2009035515 A1 | 3/2009 |
| WO | 2009070697 A2 | 6/2009 |
| WO | 2009070705 A2 | 6/2009 |
| WO | 2009070709 A1 | 6/2009 |
| WO | 2009070715 A2 | 6/2009 |
| WO | 2009070719 A1 | 6/2009 |
| WO | 2009070738 A1 | 6/2009 |
| WO | 2009110935 A1 | 9/2009 |
| WO | 2009111012 A1 | 9/2009 |
| WO | 2009015104 A2 | 12/2009 |
| WO | 2010002936 A2 | 1/2010 |
| WO | 2010022071 A2 | 2/2010 |
| WO | 2010124321 A1 | 11/2010 |

OTHER PUBLICATIONS

Vetter, R., et al., Chronic Neural Recording Using Silicon-Substrate Microelectrode Arrays Implanted in Cerebral Cortex, IEEE Transactions on Biomedical Engineering, vol. 51, No. 6, Jun. 2004, pp. 896-904.

Foreign Communication From a Related Counterpart Application—International Search Report, PCT/US2008/068165, dated Dec. 24, 2008, 3 pages.

Foreign Communication From a Related Counterpart Application—International Search Report, PCT/US2008/084898, dated May 26, 2009, 6 pages.

Foreign Communication From a Related Counterpart Application—Written Opinion PCT/US2008/084898, dated May 26, 2009, 5 pages.

Foreign Communication From a Related Counterpart Application—International Search Report, PCT/US2009/049321, dated Feb. 9, 2010, 8 pages.

Foreign Communication From a Related Counterpart Application—Written Opinion, PCT/US2009/049321, dated Feb. 9, 2010, 4 pages.

Foreign Communication From a Related Counterpart Application—Office Action dated Jul. 6, 2010, Australian Application No. 2008329642, 2 pages.

Foreign Communication From a Related Counterpart Application—Office Action dated Jul. 6, 2010, Australian Application No. 2008329648, 2 pages.

Foreign Communication From a Related Counterpart Application—Office Action dated Jul. 6, 2010, Australian Application No. 2008329652, 2 pages.

Foreign Communication From a Related Counterpart Application—Office Action dated Jul. 6, 2010, Australian Application No. 2008329671, 2 pages.

Foreign Communication From a Related Counterpart Application—Office Action dated Jul. 6, 2010, Australian Application No. 2008329716, 2 pages.

Foreign Communication From a Related Counterpart Application—Office Action dated Jul. 6, 2010, Australian Application No. 2008329724, 2 pages.

Foreign Communication From a Related Counterpart Application—Office Action dated Jul. 6, 2010, Australian Application No. 2008352005, 2 pages.

Office Action dated Feb. 24, 2011, 7 pages, U.S. Appl. No. 12/323,854, filed Nov. 26, 2008.

Cauller, Lawrence J.; U.S. Appl. No. 12/611,105; Title: "Short—Pulse Neural Stimulation Systems, Devices and Methods", filed Nov. 18, 2009; Specification 10 pgs.; 3 Drawing Sheets (Figs. 1-7).

Cauller, Lawrence J.; U.S. Appl. No. 12/611,110; Title: "Parasthesia Using Short-Pulse Neural Stimulation Systems, Devices and Methods", filed Nov. 2, 2009; Specification 10 pages; 3 Drawing Sheets (Figs. 1-7).

Office Action dated Mar. 10, 2011, 10 pages, U.S. Appl. No. 12/485,040, filed Jun. 15, 2009.

Foreign Communication from a Related Counterpart Application—Office Action dated Apr. 13, 2011, German Application No. 112008003184.3.

Office Action dated Apr. 19, 2011, 8 pages, U.S. Appl. No. 12/323,952, filed Nov. 26, 2008.

Office Action dated Apr. 28, 2011, 8 pages, U.S. Appl. No. 12/324,000, filed Nov. 26, 2008.

Office Action dated May 5, 2011, 8 pages, U.S. Appl. No. 12/485,860, filed Jun. 16, 2009.

Bohotin, C., Scholsem, M., Bohotin, V., Franzen, R. and Schoenen, J., "Vagus Nerve Stimulation Attenuates Hear- and Formalin-Induced Pain in Rats", Neuroscience Letters, 2003, vol. 351, pp. 79-82.

Bohotin, C., Scholsem, M., Multon, S., Martin, D., Bohotin, V., Schoenen, J., Vagus Nerve Stimulation in Awake Rats Reduces Formalin-Induced Nociceptive Behavior and Fos-Immunoreactivity in Trigeminal Nucleus Caudalis, Pain 101, 2003, pp. 3-12.

Burridge, J. and Etherington, R., "A Preliminary Clinical Study using RF BION Microstimulators to Facilitate Upper Limb Function in Hemiplegia", Advances in Clinical Neurosciences and Rehabilitation, May/Jun. 2004, vol. 4, pp. 26-27.

Cauller, L. and Lee, J., "In Vivo Tests of Switched-Capacitor Neural Stimulation for Use in Minimally-Invasive Wireless Implants", IEEE International Symposium on Circuits and Systems, 2008, 2 pages.

Chuang, H., "Numerical Computation of Fat Layer Effects on Microwave Near-Field Radiation to the Abdomen of a Full-Scale Human Body Model", IEEE Transactions on Microwave Theory and Techniques, vol. 45, Jan. 1997, pp. 118-125.

Cogan, S., "Neural Stimulation and Recording Electrodes" Annual Review of Biomedical Engineering, vol. 1, 2008, pp. 275-309.

Ghovanloo, M., "A Switched-Capacitor Based Neurostimulating System for Low-Power Wireless Microstimulating Systems", IEEE International Symposium on Circuits and Systems, May 2006, pp. 2197-2200.

Gopalkrishnan, P. and Sluka, K., "Effect of Varying Frequency, Intensity, and Pulse Duration of Transcutaneous Electrical Nerve Stimulation on Primary Hyperalgesia in Inflamed Rats", The American Congress of Rehabilitation Medicine and the American Academy of Physical Medicine and Rehabilitation, vol. 81, Jul. 2000, pp. 984-990.

Goroszeniuk, T., Kothari, S. and Hamann, W., "Subcutaneous Neuromodulating Implant Targeted at the Site of Pain", Regional Anesthesia and Pain Medicine, vol. 31, No. 2, Mar./Apr. 2006, pp. 168-171.

Huang et al., "A 0.5-mW Passive Telemetry IC for Biomedical Applications", IEEE Journal of Solid-State Circuits, vol. 33, No. 7, Jul. 1998, pp. 937-946.

Kilgore, K., Bhadra, N. and Snyder, J., "Treatment of Neuroma Pain Using High Frequency Alternating Current" poster, 1 page.

Li, C., and Bak, A., "Excitability Characteristics of the A- and C-Fibers in a Peripheral Nerve", Experimental Neurology, vol. 50, 1976, pp. 67-79.

Mendlin, A., Martin F.J., A. and Jacobs, B., "Dopaminergic Input is Required for Increases in Serotonin Output Produced by Behavioral Activation: An In Vivo Microdialysis Study in Rat Forebrain", Neuroscience, vol. 93, No. 3, 1999, pp. 897-905.

Millard, R. and Shepherd, R., "A Fully Implantable Stimulator for use in Small Laboratory Animals", Journal of Neuroscience Methods, 2007, pp. 168-177.

Mokwa et al., "Micro-Transponder Systems for Medical Applications", IEEE Transactions on Instrumentation and Measurement, vol. 50, No. 6, Dec. 2001, pp. 1551-1555.

Nair, S.G. and Gudelsky, G.A., "Effect of a Serotonin Depleting Regimen of 3, 4-Methylenedioxymethamphetamine (MDMA) on the Subsequent Stimulation of Acetylcholine Release in the Rat Prefrontal Cortex", Elsevier Brain Research Bulletin 69, Jan. 23, 2006, pp. 382-387.

Parikh, V., Pomerleau, F., Huettl, P, Gerhardt, G., Sarter, M. and Bruno, J.P., "Rapid Assessment of in Vivo Cholinergic Transmission by Amperometric Detection of Changes in Extracellular Choline Levels", European Journal of Neuroscience, vol. 20, Jul. 12, 2004, pp. 1545-1554.

Rainov, N., Fels, C., Heidecke, V. and Burkert, W., "Epidural Electrical Stimulation of the Motor Cortex in Patients with Facial Neuralgia", Clinical Neurology and Neurosurgery 99, 1997, pp. 205-209.

Saito, Y., Matida. S., Anami, S. Baba, H., Kinbara, A., Horikoshi, G., and Tanaka, J., "Breakdown of Alumina RF Windows", American Institute of Physics, Rev. Sci. Instrum., vol. 60, No. 7, Jul. 1989, pp. 1736-1740.

Sakai, Y., Nishijima, Y., Mikuni, N. and Iwata, N., "An Experimental Model of Hyper-Irritability in The Trigeminal Skin Field of the Rat", PAIN, vol. 7, 1979, pp. 147-157.

Sandkuhler, J., Chen, J., Cheng, G. and Randic, M., "Low-Frequency Stimulation of Afferent Aδ-Fibers Induces Long-Term Depression at Primary Afferent Synapses with Substantia Gelatinosa Neurons in the Rat", The Journal of Neuroscience, vol. 17, Issue 16, Aug. 15, 1997, pp. 6473-6491.

Sandkuhler, J., "Understanding LTP in Pain Pathways", Molecular Pain, vol. 3, Issue 9, Apr. 3, 2007, pp. 1-9.

Sheng, L., Nishiyama, K., Honda, T., Sugiura, M., Yaginuma, H. and Sugiura, Y., "Suppressive Affects of Neiting Acupuncture on Toothache: An Experimental Analysis on Fos Expression Evoked by Tooth Pulp Stimulation in the Trigeminal Subnucleus Pars Caudalis and the Periaqueductal Gray of Rats", Neuroscience Research, vol. 38, 2000, pp. 331-339.

Simpson, J. and Ghovanloo, M., "An Experimental Study of Voltage, Current, and Charge Controlled Stimulation Front-End Circuitry", IEEE International Symposium on Circuits and Systems, May 2007, pp. 325-328.

Simpson, J., Krishnamurthy, G., Feller, G., Murrow, R., and Ghovanloo, M., "A Switched-Capacitor Based Neurostimulating System for Low-Power Head-Mounted Deep Brain Stimulators", NCBIONICS, North Carolina State University, 1 page.

Spinner, R., "Outcomes for Peripheral Entrapment Syndromes", Clinical Neurosurgery, vol. 53, 2006, pp. 285-294.

Tsodyks, M., "Computational neuroscience grand challenges—a humble attempt at future forecast", Frontiers in Neuroscience, vol. 2, Jul. 2008, pp. 17-18.

Vuckovic, A. and Rijkhoff, N., "Different Pulse Shapes for Selective Large Fibre Block in Sacral Nerve Roots Using a Technique of Anodal Block: An experimental Study" Medical & Biological Engineering & Computing, vol. 42, 2004, pp. 817-824.

Wever, R. and Hemrika, W., "Vanadium Haloperoxidases", Handbook of Metalloproteins, John Wiley & Sons, Ltd. Chichester, 2001, pp. 1416-1428.

EZstim II Peripheral Nerve Locator and Stimulator, Model ES400, Operator's Manual, Life-Tech, Inc., 2005, 29 pages.

"Multi-Program Neurostimulator", Implant Manual, Medtronic, 2006, 16 pages.

"Stimuplex Nerve Stimulator" brochure, Braun, 4 pages.

Office Action dated Aug. 19, 2010, 8 pages, U.S. Appl. No. 12/323,854, filed Nov. 26, 2008.

Office Action dated Dec. 22, 2010, 11 pages, U.S. Appl. No. 12/323,904, filed Nov. 26, 2008.

Office Action dated Dec. 2, 2010, 9 pages, U.S. Appl. No. 12/323,934, filed Nov. 26, 2008.

Office Action dated Oct. 4, 2010, 11 pages, U.S. Appl. No. 12/323,952, filed Nov. 26, 2008.

Office Action dated Jul. 9, 2010, 18 pages, U.S. Appl. No. 12/323,952, filed Nov. 26, 2008.

Office Action dated Jan. 19, 2011, 11 pages, U.S. Appl. No. 12/323,969, filed Nov. 26, 2008.

Office Action dated Aug. 30, 2010, 5 pages, U.S. Appl. No. 12/323,969, filed Nov. 26, 2008.

Office Action dated Dec. 9, 2010, 7 pages, U.S. Appl. No. 12/324,000, filed Nov. 26, 2008.

Engineer, et al., "Reversing Pathological Neural Activity Using Targeted Plasticity," Nature, vol. 47, Feb. 3, 2011, pp. 101-106.

Arthur, D.W. et al., "Improvements in Critical Dosimetric Endpoints Using the Contura Multilumen Ballon Breast Brachytherapy Catheter to Deliver Accelerated Partial Breast Irradiation: Preliminary Dosimetric Findings of a Phase IV Trial," Int. J. Radiation Oncology Biol. Phys., vol. 79, No. 1, 2011, pp. 26-33.

Atluri, S. et al., "Design of a Wideband Power-Efficient Inductive Wireless Link for Implantable Biomedical Devices Using Multiple Carriers," Proceedings of the International IEEE EMBS Conference on Neural Engineering Arlington, Virginia, Mar. 16-19, 2005, http://www.ece.ncsu.edu/erl/html2/papers/ghovanloo/2005/ghovanloo_2005_atluri.pdf.

Asgarian, F. et al., "Wireless Telemetry for Implantable Biomedical Microsystems," Integrated Circuits and Systems (ICAS) Lab., Department of Electrical and Computer Eng., K.N. Toosi University of Technology, www.intechopen.com/download/pdf/pdfs_id/12899.

Avitall, B. et al., "Physics and Engineering of Transcatheter Cardiac Tissue Ablation," Journal of the American College of Cardiology, vol. 22, No. 3, Sep. 1993, pp. 921-932.

Cavalcanti, A. et al., "Nanorobot for Treatment of Patients with Artery Occlusion," Proceedings of Virtual Concept, 2006, 10 pages.

Chaimanonart, N. et al., "Adaptive RF Power for Wireless Implantable Bio-Sensing Network to Monitor Untethered Laboratory Animal Real-Time Biological Signals," IEEE Sensors, Oct. 2008, pp. 1241-1244, Abstract.

Chandrakasan, AP et al., "Ultra-Power Electronics for Biomedical Applications", Annual Rev. Biomed. Eng., 2008, Abstract.

Cheung, K.C., "Implantable Microscale Neural Interfaces," Biomed Microdevices, Dec. 2007, pp. 923-938, Abstract.

Citro, R. et al., "Intracardiac Echocardiography to Guide Transseptal Catheterization for Radiofrequency Catheter Ablation of Left-Sided Accessory Pathways: two case reports," Cardiovascular Ultrasound, 2004, 7 pages.

Clark, et al., "Enhanced Recognition Memory Following Vagus Nerve Stimulation in Human Subjects," Nature Neuroscience, vol. 2, No. 1, Jan. 1999, pp. 94-98.

Dimyan, M.A. et al, "Neuroplasticity in the Context of Motor Rehabilitation After Stroke," Nat. Rev. Neurol. Feb. 2011, Review. http://www.nature.com/nrneurol/journal/v7/n2/abs/nrneurol.2010.200. html?http://www.ncbi.nlm.nih.gov/pubmed/21243015.

Fotopoulou, K. et al., "Wireless Powering of Implanted Sensors Using RF Inductive Coupling," 5th IEEE Conference on Sensors, Oct. 2006, pp. 765-768, Abstract.

George, M.S. et al., "Vagus Nerve Stimulation: A New Tool for Brain Research and Therapy," Biol Psychiatry, 2000, pp. 287-295. http://www.ncbi.nlm.nih.gov/pubmed/10686263.

Gimsa, J. et al., "Choosing Electrodes for Deep Brain Stimulation Experiments—Electrochemical Considerations," J Neurosci. Methods, Mar. 30, 2005, Abstract.

Hijazi, N. et al., "Wireless Power and Data Transmission System for a Micro Implantable Intraocular Vision Aid," Biomed Tech (Berl), 2002; 47 Suppl 1 Pt1:174-5, Abstract.

Kim, S. et al., "Influence of System Integration and Packaging for a Wireless Neural Interface on its Wireless Powering Performance," 30th Annual International Conference of the IEEE Engineering in Medicine and Biology Society, Aug. 2008, pp. 3182-3185, Abstract.

Laskovski, A. et al., "Wireless Power Technology for Biomedical Implants," University of Newcastle, Australia, www.intechopen.com/download/pdf/pdfs_id/8797, Oct. 2009.

Loeb, G.E. et al., "RF-Powered BIONs for Stimulation and Sensing," 26th Annual International Conference of the IEEE Engineering in Medicine and Biology Society, 2004, vol. 2, p. 4182, Abstract.

Lu, HM et al., "MEMS-Based Inductively Coupled RFID Transponder for Implantable Wireless Sensor Applications," IEEE Transactions on Magnetics, vol. 43, No. 6, Jun. 2007, pp. 2412-2414.

Mokwa et al., "Intraocular Epiretinal Prosthesis to Restore Vision in Blind Humans," 30th Annual International Conference of the IEEE Engineering in Medicine and Biology Society, Aug. 2008, p. 5790, Abstract.

Mouine, J. et al., "A Completely Programmable and Very Flexible Implantable Pain Controller," Proc. of the 22nd Annual Intern Conference of the IEEE, vol. 2, 2000, pp. 1104-1107, Abstract.

Mounaim, F. et al., "Miniature Implantable System Dedicated to Bi-Channel Selective Neurostimulation," IEEE International Symposium on Circuits and Systems, 2007, pp. 2072-2075, Abstract.

Myers, F.B. et al., "A Wideband Wireless Neural Stimulation Platform for High-Density Microelectrode Arrays," 28th Annual International Conference of the IEEE Engineering in Medicine and Biology Society, Aug. 30, 2006, pp. 4404-4407, Abstract.

Papazoglou, C. et al., "Endoluminal Grafting: The Arizona Heart Institute Experience," International Congress VIII on Endovascular Interventions, Breaking Barriers, Scottsdale, Arizona, Feb. 12-16, 1995, pp. 89-129.

Peters, T.K. et al., "The Evolution Strategy—A Search Strategy Used in Individual Optimization of Electrica Therapeutic Carotid Sinus Nerve Stimulation," IEEE Transactions on Biomedical Engineering, vol. 36, Issue 7, pp. 668-675, Abstract http://ieeexplore.ieee.org/search/srchabstract.jsp?tp=&arnumber=32098&queryText%3D%28Implant+And+induction%29+AND+%28antenna+OR+coil%29+AND+%28t%29%26searchWit, Abstract, 1989.

Popovic, D.B. et al., "Electrical Stimulation as a Means for Achieving Recovery of Function in Stoke Patients," NeuroRehabilitation, vol. 1, 2009, pp. 45-58. Abstract http://www.ncbi.nlm.nih.gov/pubmed/19713618.

Sawan, M., "Medical Microsystems for the Recovery of Vital Neural Functions," ncku.edu.tw polystim neurotechnologies Tianan, Taiwan, http://www.google.com/url?sa=t&source=web&cd=1&ved=0CBcQFjAA&url=http% 3A%2F%2Ford.ncku.edu.tw%2Fezfiles%2F3%2F1003%2Fimg%2F467%2F20080911_ppt.pdei=elayTZeNO-Ls0gHW7IHCCw&usg=AFQjCNE8HVhoI0Y63ztvd1sxK8-8aDdLAw&sig2=c7qWn1zQ2QUrwRMDvC53Gw.

Sawan, M., "Wireless Smart Implants Dedicated to Multichannel Monitoring and Microstimulation," IEEE/ACS International Conference on Pervasive Services, Jul. 2004, pp. 21-26, Abstract.

Schwiebert, L. et al., "Research Challenges in Wireless Networks of Biomedical Sensors," Disclosing for maximizing signal distance/minimizing power with multiple implant arrays in section 5.1, pp. 159-161, 2001.

Shabou, S. et al., "The RF Circuit Design for Magnetic Power Transmission Dedicated to Cochlear Prosthesis," 12th IEEE International Conference on Electronics, Circuits and Systems, 2005, pp. 1-4, Abstract.

Sharma, N. et al., "Electrical Stimulation and Testosterone Differentially Enhance Expression of Regeneration-Associated Genes," Exp Neurol., vol. 1, May 2010, pp. 183-191, Abstract.

Shepherd, RD et al., "Electrical Stimulation of the Auditory Nerve: II. Effect of Stimulus Waveshape on Single Fibre Response Properties," Hear Res., vol. 130, Apr. 1999, pp. 171-188, Abstract.

Sit, Ji-Jon et al., "A Low-Power Blocking-Capacitor-Free Charge-Balanced Electrode-Stimulator Chip with Less Than 6 nA DC Error for 1-mA Full-Scale Stimulation," IEEE Transactions on Biomedical Circuits and Systems, vol. 1, No. 3, Sep. 2007, pp. 172-183.

Sooksood, K., et al., "Recent Advances in Charge Balancing for Functional Electrical Stimulation", Conf. Proc. IEEE Eng. Med. Biol. Soc., Nov. 13, 2009, Abstract.

Sooksood, K., et al., "An Experimental Study on Passive Charge Balancing," Adv. Radio Sci., vol. 7, 2009, pp. 197-200.

Suaning, G.J. et al., "CMOS Neurostimulation ASIC with 100 Channels, Scaleable Output, and Bidirectional Radio-Frequency," Biomedical Engineering, IEEE Transactions on Biomedical Engineering, vol. 48, Issue 2, pp. 248-260, Abstact, Feb. 2001.

Van Greevenbroek, B., "The Development of Neuro-Prosthetic Devices," Feb. 10, 2011, http://www.google.com/url?sa=t&source=web&cd=17&ved=0CH4QFjAQ&url=http%3A%2F%2Figitur-archive.library.uu.nl%2Fstudent-theses%2F2011-0210-200413%2520development%2520of%252Neuro-Prosthetic%2520Devices%2520(Pdf%2520af).pdf%ei=rUeuTeTMN6W60QGt1bWq.

Van Wieringen A. et al., "Effects of waveform Shape on Human Sensitivity to Electrical Stimulation of the Inner Ear," Hear Res., Feb. 2005, Abstract.

Venkataraman, S. et al., "RF-Front End for Wireless Powered Neural Applications," 51st Midwest Symposium Circuits and Systems, Aug. 2008, pp. 682-685, Abstract.

Wise, K.D. et al., "Wireless implantable Microsystems: High-Density Electronic Interfaces to the Nervous System," Proceedings of the IEEE, vol. 92, Issue 1, Jan. 2004, pp. 76-97, Abstract.

Xing et al., "Research Progress of Subrentinal Implant Based on Electronic Stimulation," Engineering in Medicine and Biology Society, 2005, pp. 1289-1292, Abstract http://ieeexplore.iee.org/search/srchabstract.jsp?queryText=%28Implant%20And%20induction%29%20AND%20%28antenna%20OR%20coil%29%20AND%20%28transfer%20OR%20relay%29%20AND%20%28multiple%20OR%20plural%20OR%20array%29%20AND%20%28medic*%20OR%20surg*%20OR%2.

Yazdandoost, KY et al., "An Antenna for Medical Implant Communications System," European Microwave Conference, 2007, pp. 968-971, Abstract.

Yekeh, K. et al., "Wireless Communications for Body Implanted Medical Device," Asia-Pacific Microwave Conference, 2007, pp. 1-4, Abstract.

Yoon, "A dual spiral antenna for Ultra-wideband capsule endoscope system," Department of Electronics and Electronic Engineering, Yonsei University Seoul, http://sciencestage.com/d/5302029/a-dual-spiral-antenna-for-ultra-widegand-capsule-endoscope-system. html, Abstract, Mar. 2008.

Zhang, YI et al., "Episodic phrenic-Inhibitory Vagus Nerve Stimulation Paradoxically Induces Phrenic Long-Term Facilitation in Rats," J Physiol., Sep. 15, 2003, pp. 981-991. Linghttp://www.ncbi.nlm.nih.gov/pmc/articles/PMC2343284.

Office Action dated Sep. 27, 2011, 7 pages, U.S. Appl. No. 12/323,854, filed Nov. 26, 2008.

Office Action dated Aug. 29, 2011, 70 pages, U.S. Appl. No. 12/323,904, filed Nov. 26, 2008.
Office Action dated Jul. 15, 2011, 36 pages, U.S. Appl. No. 12/323,934, filed Nov. 28, 2008.
Office Action dated Sep. 26, 2011, 17 pages, U.S. Appl. No. 12/324,000, filed Nov. 26, 2008.
Office Action dated Oct. 25, 2011, 15 pages, U.S. Appl. No. 12/485,040, filed Jun. 15, 2009.
Office Action dated Jan. 3, 2012, 9 pages, U.S. Appl. No. 12/485,860, filed Jun. 16, 2009.
Office Action dated Oct. 28, 2011, 17 pages, U.S. Appl. No. 12/558,734, filed Sep. 14, 2009.
Office Action dated Aug. 23, 2011, 4 pages, U.S. Appl. No. 12/624,383, filed Nov. 23, 2009.
Foreign Communication From a Related Counterpart Application—International Search Report, PCT/US2010/058737 dated Aug. 31, 2011, 7 pages.
Foreign Communication From a Related Counterpart Application—Written Opinion PCT/US2010/058737 dated Aug. 31, 2011, 8 pages.
Foreign Communication from a Related Counterpart Application—Office Action dated Jun. 15, 2011, German Application No. 112008003183.5.
Office Action dated Jun. 5, 2012, 38 pages, U.S. Appl. No. 12/485,860, filed Jun. 16, 2009.
Office Action dated Aug. 1, 2011, 9 pages, U.S. Appl. No. 12/324,044, filed Nov. 26, 2008.

* cited by examiner

TIMING CONTROL FOR PAIRED PLASTICITY

PRIORITY CLAIM

This application is a continuation application of U.S. Utility patent application Ser. No. 12/485,040, filed Jun. 15, 2009 and claims priority benefits under 35 U.S.C. §119(e) from U.S. Provisional Application No. 61/077,648, filed on Jul. 2, 2008 and entitled "Treatment of Tinnitus with Vagus Nerve Stimulation"; U.S. Provisional Application No. 61/078,954, filed on Jul. 8, 2008 and entitled "Neuroplasticity Enhancement"; U.S. Provisional Application No. 61/086,116, filed on Aug. 4, 2008 and entitled "Tinnitus Treatment Methods and Apparatus"; and U.S. Provisional Application No. 61/149,387, filed on Feb. 3, 2009 and entitled "Healing the Human Brain: The Next Medical Revolution." The present application incorporates the foregoing disclosures herein by reference.

BACKGROUND

The present disclosure relates generally to therapy, rehabilitation and training including induced plasticity. More particularly, the disclosure relates to methods and systems of enhancing therapy, rehabilitation and training using nerve stimulation paired with training experiences.

SUMMARY

For purposes of summarizing the invention, certain aspects, advantages, and novel features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

The disclosed inventions will be described with reference to the accompanying drawings, which show important sample embodiments of the invention and which are incorporated in the specification hereof by reference, wherein.

DETAILED DESCRIPTION OF THE DRAWINGS

The numerous innovative teachings of the present application will be described with particular reference to presently preferred embodiments (by way of example, and not of limitation). The present application describes several inventions, and none of the statements below should be taken as limiting the claims generally. Where block diagrams have been used to illustrate the invention, it should be recognized that the physical location where described functions are performed are not necessarily represented by the blocks. Part of a function may be performed in one location while another part of the same function is performed at a distinct location. Multiple functions may be performed at the same location.

Figure 1:
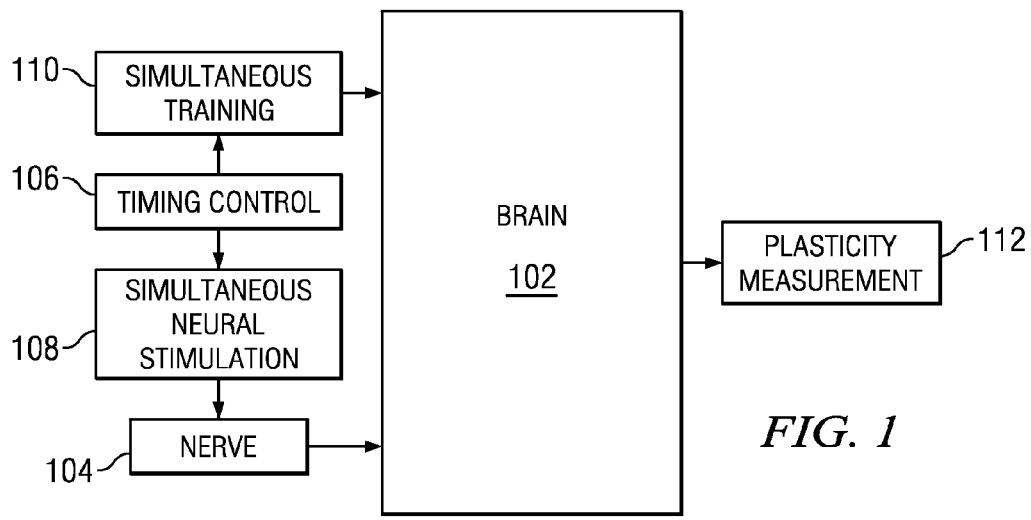
FIG. 1 is a block diagram depicting a paired training system, in accordance with an embodiment.

With reference to FIG. 1, a paired training system is shown. A timing control system 106 is communicably connected to a neural stimulator system 108 and a training system 110. Receiving timing instruction from the timing control system 106, the neural stimulator system 108 provides stimulation to a nerve 104. Similarly receiving timing instruction from the timing control system 106, or providing timing instruction to the timing control system 106, the training system 110 generates desired mental images, ideas, formations or states in the brain 102. The stimulation of the nerve 104 affects the brain 102 by inducing plasticity. The temporally paired combination of training and stimulation generates manifestations of plasticity in the brain 102 that may be measured by a plasticity measure system 112.

The timing controls system 106 generally provides the simultaneous nature of the pairing. The stimulation and the training are simultaneous in that they occur at the same time, that is, there is at least some overlap in the timing. In some embodiments, the stimulation may lead the start of the training while in other embodiments, the stimulation may follow the start of the training. In many cases, the stimulation is shorter in duration than the training, such that the stimulation occurs near the beginning of the training. Plasticity resulting from stimulation has been shown to last minutes or hours, so a single stimulation pulse may suffice for the whole duration of extended training.

In the treatment of tinnitus, for example, the training may consist of brief audible sounds including selected therapeutic frequencies, paired with stimulations. Because the duration of the sounds may be short, the timing may be controlled very precisely so that the sound coincides temporally with the stimulation. This kind of precision may typically require some form of computer control. In other forms of rehabilitation or education, the timing of the training and/or the stimulation may be controlled manually. Further therapies and training may include training triggered timing or physical condition feedback to provide a closed-loop system.

The neural stimulation system 108 may provide stimulation of the nerve 104 using electrical stimulation, chemical stimulation, magnetic stimulation, optical stimulation, mechanical stimulation or any other form of suitable nerve stimulation. In accordance with an embodiment, an electrical stimulation is provided to the left vagus nerve. In an electrical stimulation system, suitable stimulation pulses may include a variety of waveforms, including constant current pulses, constant voltage pulses, exponential pulses or any other appropriate waveform. An electrical stimulation system may use a single stimulation pulse or a train of stimulation pulses to stimulate the nerve 104. Stimulation parameters are selected to affect the brain 102 appropriately, with reference to the affected brain regions or systems, plasticity measures, desynchronization or any other appropriate stimulation parameter measure. A half second train of biphasic stimulation pulses, with a pulse width of 100 microseconds, at 0.8 milliamps and at 30 Hz has been used effectively in the treatment of tinnitus.

Paired stimulation could be accomplished using deep brain stimulation, cortical stimulation, transcranial magnetic stimulation and any other suitable neural stimulation.

One indication of appropriate stimulation may be desynchronization of the cortical EEG. A 0.8 milliamp pulse has been shown to cause cortical desynchronization at frequencies between 30 and 150 Hz. 0.4 milliamp pulses desynchronize the cortex at higher frequencies of 100 to 150 Hz. Desynchronization has been shown to last for at least four seconds in response to stimulation of the vagus nerve.

The simultaneous training system 110 generates the sensory input, motor sequences, cognitive input, mental images, ideas, formations or states that are to be retained by the brain 102. A training system 110 may provide sensory information, such as visual, auditory, olfactory, tactile or any other suitable sensory information. Training system 110 may include physical therapies, cognitive therapies, emotional therapies, chemical therapies, or any other suitable therapies. Training system 110 may present educational information. Training system 110 may include the subject, physically, mentally, emotionally or in any other suitable fashion. Training system 110 may include teachers, doctors, therapists, counselors, instructors, coaches or any other suitable training provider. Training system 110 may evoke specific patterns of neural activity by direct brain stimulation, for example by electrical, magnetic, optical, or any other suitable pattern evocation systems. Training system 110 may inactivate specific brain regions via chemical agents, cooling, magnetic stimulation, or other suitable methods.

The paired training system of FIG. 1 affects the brain 102 to generate plasticity that can be measured by a plasticity measure system 112. In the treatment of tinnitus, a cortical map may be used to measure the map distortion and correction that accompanies the successful treatment of tinnitus. Less invasively, the plasticity can be measured by behaviorally reactions to stimuli, such as a startle test for tinnitus. Further, plasticity can be measured by inquiring about the subjective experience of a subject. If a tinnitus patient no longer experiences a persistent noise, plasticity has been measured.

Figure 2:
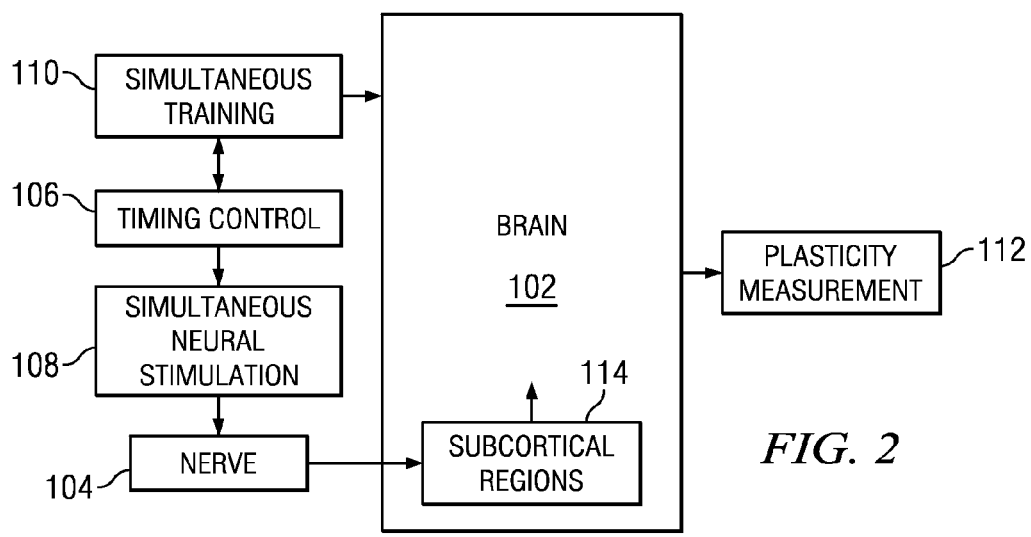
FIG. 2 is a block diagram depicting a paired training system affecting a subcortical region, in accordance with an embodiment.

With reference to FIG. 2, a paired training system affecting a subcortical region 114 of the brain 102, in accordance with an embodiment is shown. The stimulation of nerve 104 affects a subcortical region 114. The subcortical region 114, in turn, affects the brain to induce plasticity. Stimulation of nerves 104 such as the trigeminal nerve and other cranial nerves are known to affect the subcortical region 114.

Figure 3:
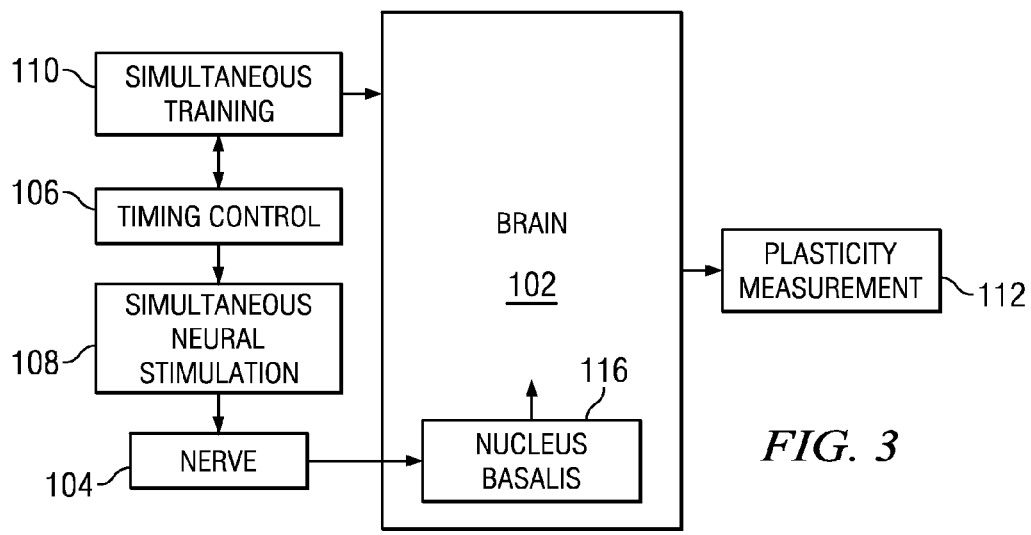
FIG. 3 is a block diagram depicting a paired training system affecting the nucleus basalis, in accordance with an embodiment.

With reference to FIG. 3, a paired training system affecting the nucleus basalis 116, in accordance with an embodiment, is shown. The stimulation of nerve 104 affects the nucleus basalis 116. The nucleus basalis, in turn, affects the brain 102 to induce plasticity.

Figure 4:
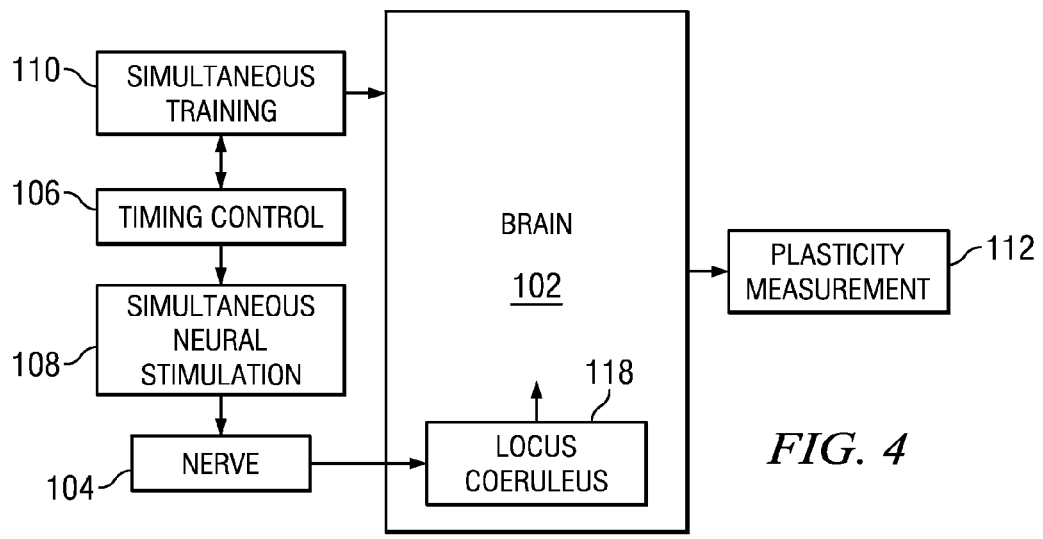
FIG. 4 is a block diagram depicting a paired training system affecting the locus coeruleus, in accordance with an embodiment.

With reference to FIG. 4, a paired training system affecting the locus coeruleus 118, in accordance with an embodiment, is shown. The stimulation of nerve 104 affects the locus coeruleus 118. The locus coeruleus 118, in turn, affects the brain 102 to induce plasticity.

Figure 5:
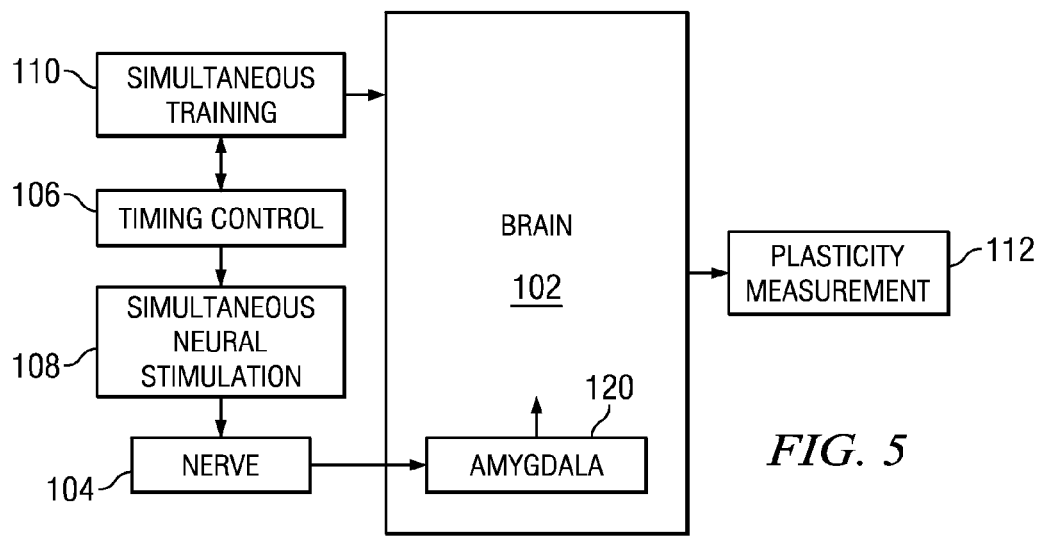
FIG. 5 is a block diagram depicting a paired training system affecting the amygdala, in accordance with an embodiment.

With reference to FIG. 5, a paired training system affecting the amygdala 120, in accordance with an embodiment, is shown. The stimulation of nerve 104 affects the amygdala 120. The amygdala 120, in turn, affects the brain 102 to induce plasticity.

Figure 6:
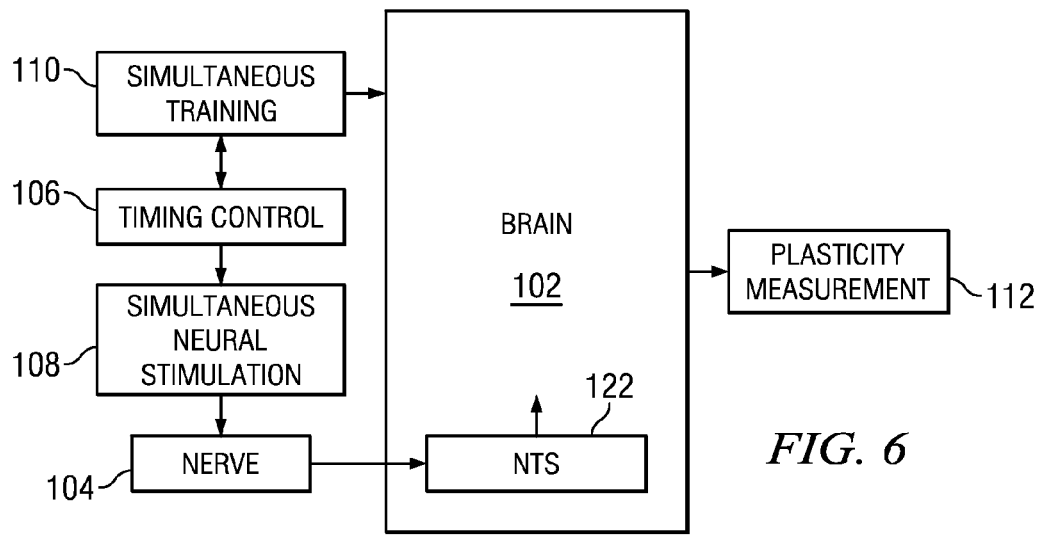
FIG. 6 is a block diagram depicting a paired training system affecting the nucleus of the solitary tract (NTS), in accordance with an embodiment.

With reference to FIG. 6, a paired training system affecting the NTS 122, in accordance with an embodiment, is shown. The stimulation of nerve 104 affects the NTS 122. The NTS 122, in turn, affects the brain 102 to induce plasticity.

Figure 7:
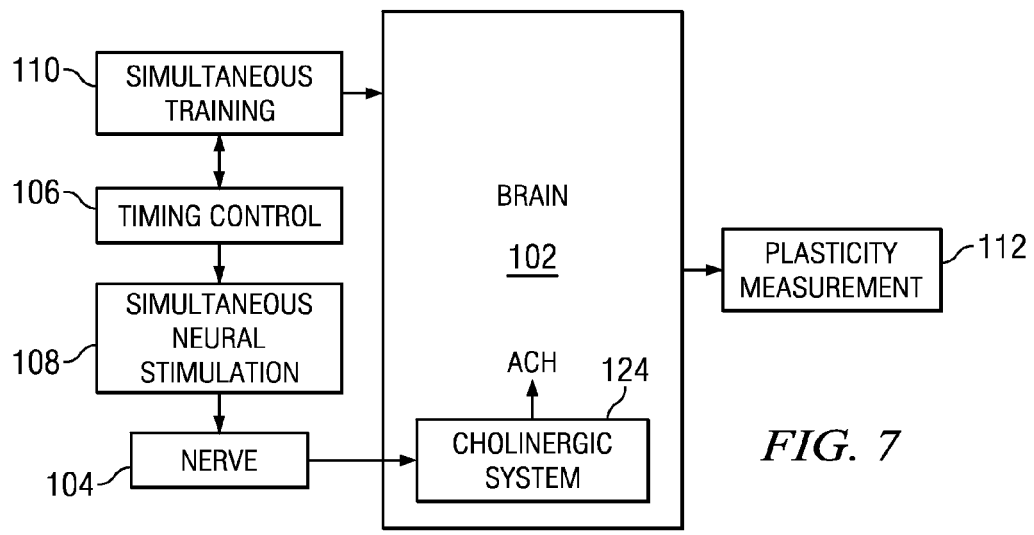
FIG. 7 is a block diagram depicting a paired training system affecting the cholinergic system, in accordance with an embodiment.

With reference to FIG. 7, a paired training system affecting the cholergenic system 124, in accordance with an embodiment, is shown. The stimulation of nerve 104 affects the cholergenic system 124. The cholergenic system 124 releases acetylcholine (ACh) into the brain 102 inducing plasticity.

Figure 8:
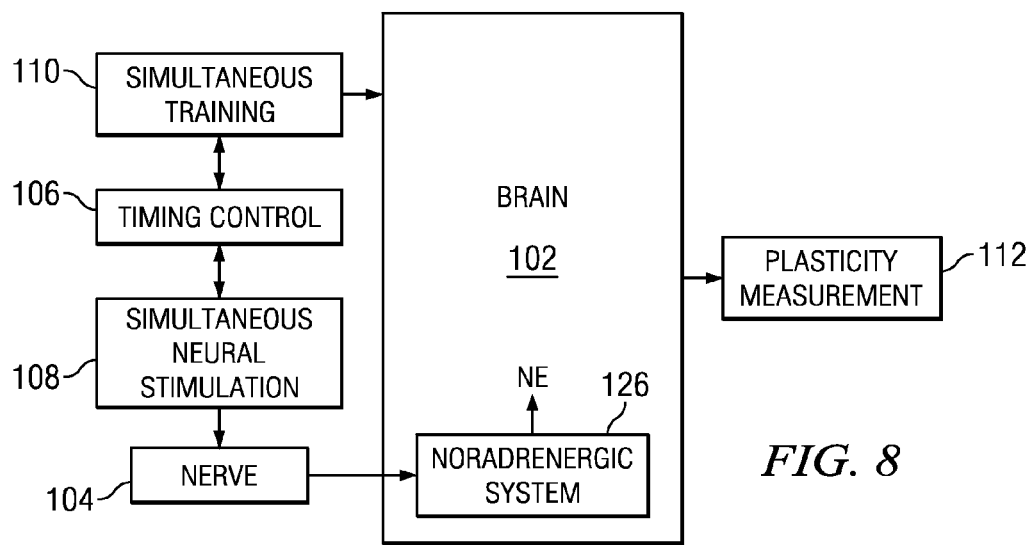
FIG. 8 is a block diagram depicting a paired training system affecting the noradrenergic system, in accordance with an embodiment.

With reference to FIG. 8, a paired training system affecting the noradrenergic system 126, in accordance with an embodiment, is shown. The stimulation of nerve 104 affects the noradrenergic system 126. The noradrenergic system 126 releases noradrenaline (NE) into the brain 102 inducing plasticity.

Figure 9:
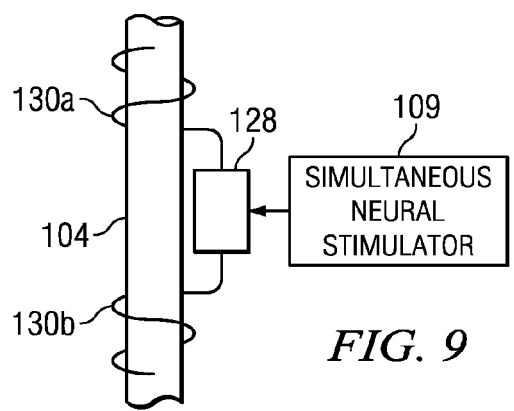
FIG. 9 is a simplified diagram depicting a stimulator, in accordance with an embodiment.

With reference to FIG. 9, a neural stimulator system, in accordance with an embodiment, is shown. A neural stimulator control 109 is communicably connected to a neurostimulator 128. Neurostimulator 128 provides a stimulation pulse to a nerve 104 via a pair of electrodes 130a and 130b. Electrodes 130a and 130b could be cuff electrodes, conductive plates or any other suitable neural stimulation electrode. The neurostimulator 128 may be powered by a piezoelectric powering system as well as near field inductive power transfer, far-field inductive power transfer, battery, rechargeable battery or any other suitable neurostimulator power system. When neural stimulator control 109 receives timing instructions from a timing control system (not shown), the neural stimulator control 109 initiates a stimulation pulse from the neurostimulator 128 via electrodes 130*a* and 130*b*.

Figure 10:
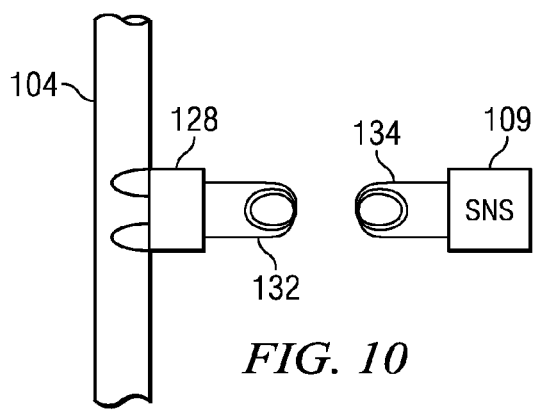
FIG. 10 is a simplified diagram depicting a wireless stimulator, in accordance with an embodiment.

With reference to FIG. 10, a wireless neural stimulator system, in accordance with an embodiment is shown. Neurostimulator 128 communicates with the neural stimulation system 109 using an inductive transponder coil 132. The neural stimulator system 109 includes an external coil 134. Information may be communicated between the neural stimulator system 109 and the neurostimulator 128. Power may be transferred to the neurostimulator 128 by the neural stimulator system.

Figure 11:
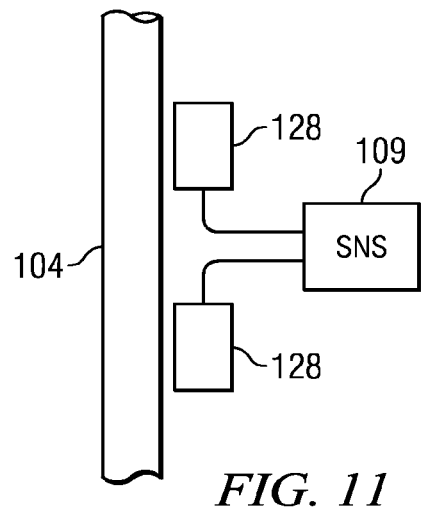
FIG. 11 is a simplified diagram depicting a dual stimulator configuration, in accordance with an embodiment.

With reference to FIG. 11, a dual neurostimulator system, in accordance with an embodiment, is shown. Two neurostimulators 128 may stimulate nerve 104. The neurostimulators 128 may be controlled to reinforce each other, as redundancy, or to prevent efferent signals from projecting away from the brain.

Figure 12:
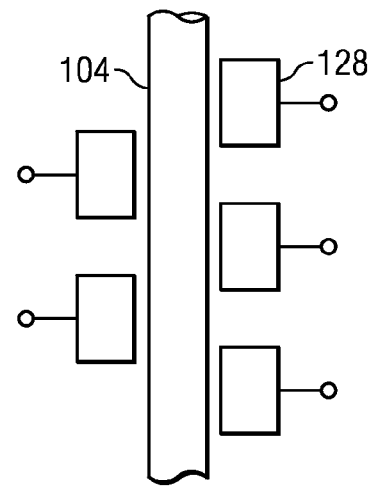
FIG. 12 is a simplified diagram depicting a multi-stimulator configuration, in accordance with an embodiment.

With reference to FIG. 12, a multi-neurostimulator system, in accordance with an embodiment, is shown. A plurality of neurostimulators 128 may stimulate nerve 104. The neurostimulators may be controlled to reinforce each other, as redundancy, or to prevent efferent signals from projecting away from the brain.

Figure 13:
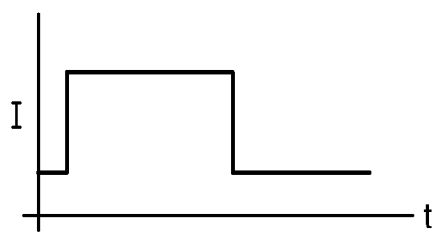
FIG. 13 is a graph depicting a constant current stimulation pulse, in accordance with an embodiment.

With reference to FIG. 13, a graph shows a constant current stimulation pulse, in accordance with an embodiment.

Figure 14:
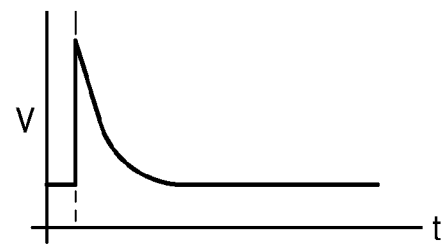
FIG. 14 is a graph depicting an exponential stimulation pulse, in accordance with an embodiment.

With reference to FIG. 14, a graph shows an exponential stimulation pulse, in accordance with an embodiment.

Figure 15:
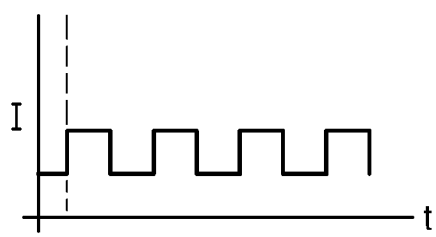
FIG. 15 is a graph depicting a train of constant current stimulation pulses, in accordance with an embodiment.

With reference to FIG. 15, a graph shows a train of constant current stimulation pulses, in accordance with an embodiment.

Figure 16:
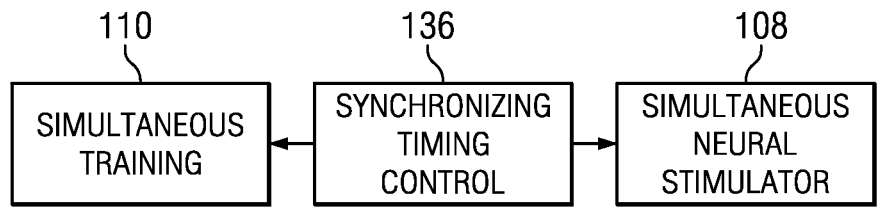
FIG. 16 is a block diagram depicting a synchronizing control system, in accordance with an embodiment.

With reference to FIG. 16, a synchronized timing control system, in accordance with an embodiment, is shown. The synchronized timing control system includes a synchronizing timing control 136. The synchronizing timing control 136 is communicably connected to the neural stimulation system 108 and the training system 110. The synchronizing timing control 136 provides timing instructions to the neural stimulation system 108 and the training system 110 so that the stimulation and training occur simultaneously. In the treatment of tinnitus, the stimulation of the nerve may slightly precede each training sound, to give the stimulation time to affect the brain when the training sound is presented. Further embodiments may include other suitable timing variations.

Figure 17:
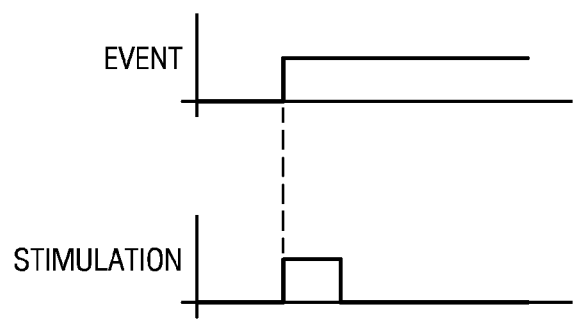
FIG. 17 is a graph depicting synchronized pairing, in accordance with an embodiment.

With reference to FIG. 17, a graph shows a possible timing relationship between event and stimulation for a synchronized timing control system.

Figure 18:
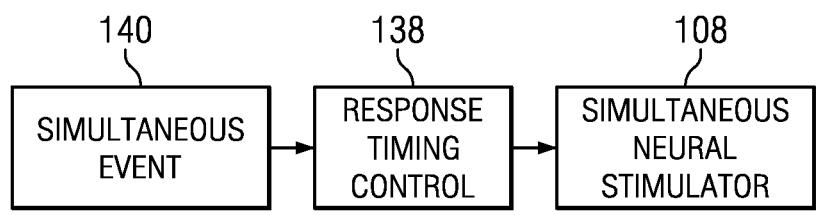
FIG. 18 is a block diagram depicting a response control system, in accordance with an embodiment.

With reference to FIG. 18, a response timing control system, in accordance with an embodiment, is shown. The response timing control system includes a response timing control 138. The response timing control 138 is communicably connected to the neural stimulation system 108 and a simultaneous event monitor 140. The response timing control 138 receives timing instructions from the event monitor 140 and provides timing instructions to the neural stimulation system 108, so that the stimulation and training occur simultaneously. Because the stimulation is generated in response to an event, the stimulation will generally lag the event by some finite time delta t. In cases where there is an event precursor that can be monitored, the timing can be made more exact.

Figure 19:
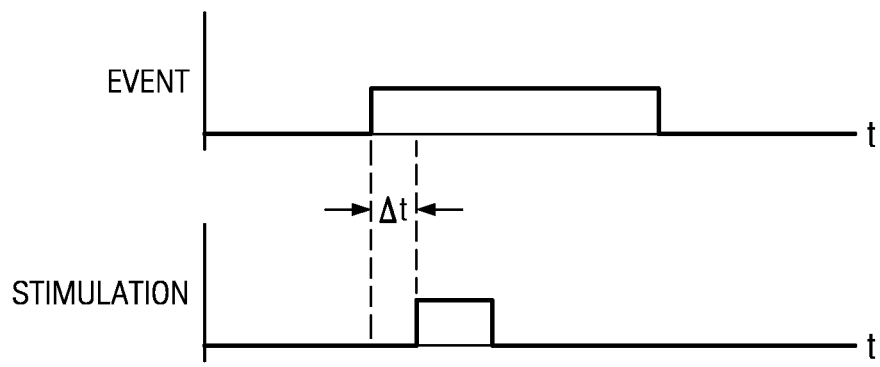
FIG. 19 is a graph depicting response pairing, in accordance with an embodiment.

With reference to FIG. 19, a graph shows a possible timing relationship between a monitored event and a nerve stimulation.

Figure 20:
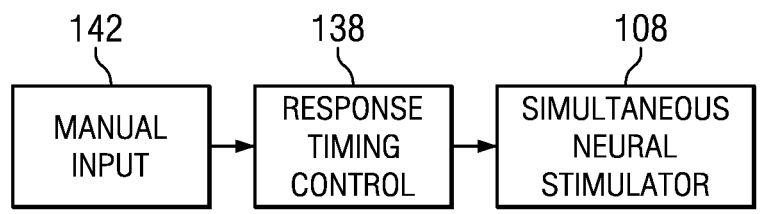
FIG. 20 is a block diagram depicting a manual control system, in accordance with an embodiment.

With reference to FIG. 20, a manual timing control system, in accordance with an embodiment, is shown. The manual timing control system includes a response timing control 138. The response timing control 138 is communicably connected to the neural stimulation system 108 and a manual input 142. The response timing control 138 receives timing instructions from the manual input 142 and provides timing instructions to the neural stimulation system 108, so that the stimulation and training occur simultaneously.

Figure 21:
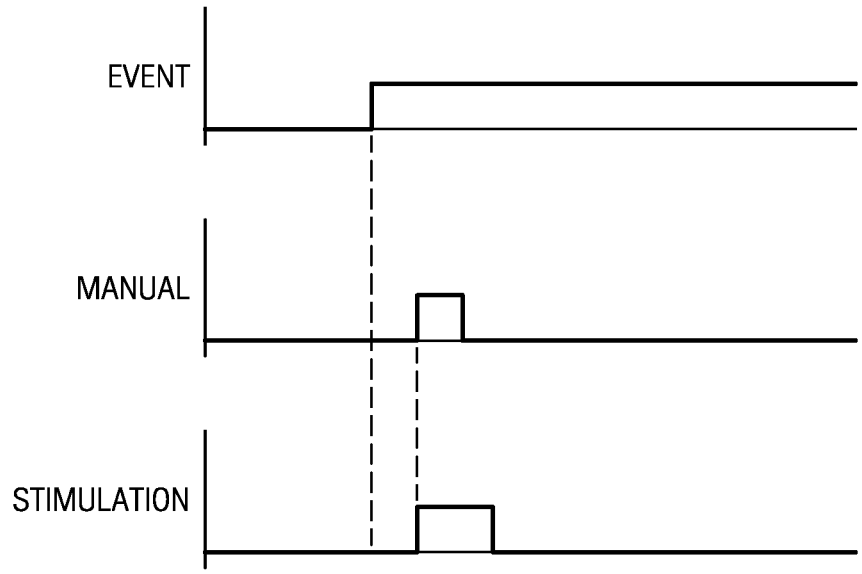
FIG. 21 is a graph depicting manual pairing, in accordance with an embodiment.

With reference to FIG. 21, a graph shows a possible timing relationship between an event, a manual input and a neural stimulation.

Figure 22:
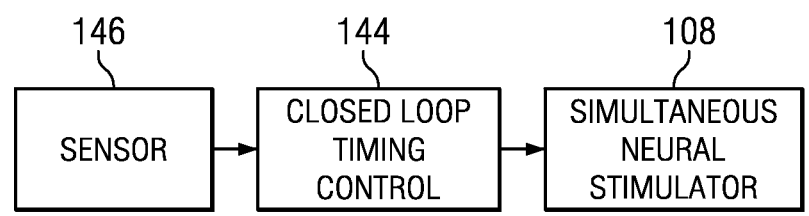
FIG. 22 is a block diagram depicting a closed loop control system, in accordance with an embodiment.

With reference to FIG. 22, a closed loop timing control system, in accordance with an embodiment, is shown. The closed loop timing control system includes a closed loop timing control 144. The closed loop timing control 144 is communicably connected to the neural stimulation system 108 and a sensor 146. The closed loop timing control 144 receives timing instructions from the sensor 146 and provides timing instructions to the neural stimulation system 108, so that the stimulation and training occur simultaneously.

Figure 23:
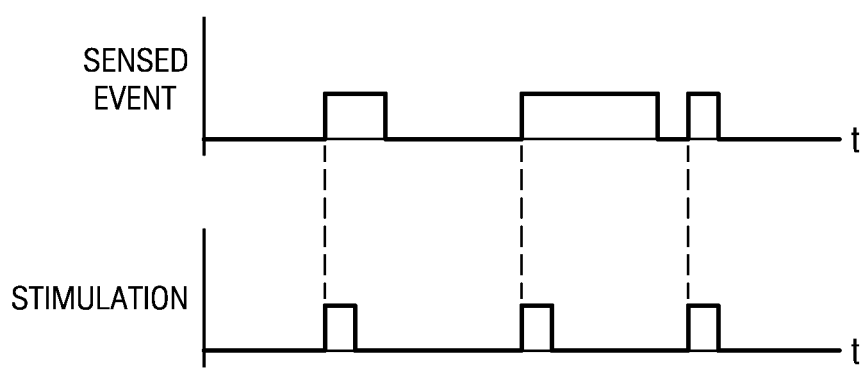
FIG. 23 is a graph depicting closed loop pairing, in accordance with an embodiment.

With reference to FIG. 23, a graph shows a possible timing relationship between an sensed training event and a neural stimulation is shown.

Sensor 146 may monitor external or internal events, including heart-rate, blood pressure, temperature, chemical levels or any other parameter that may indicate a training event.

Figure 24:
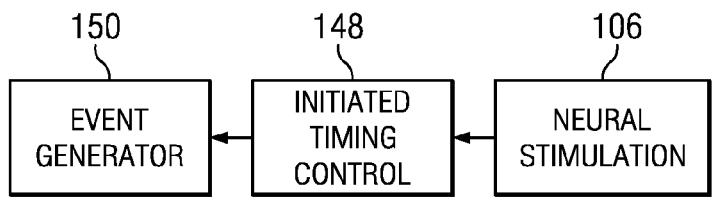
FIG. 24 is a block diagram depicting an initiated control system, in accordance with an embodiment.

With reference to FIG. 24, a initiated timing control system, in accordance with an embodiment, is shown. The initiated timing control system includes an initiated timing control 148. The initiated timing control 148 is communicably connected to a neural stimulation system 106 and an event generator 150. The initiated timing control 148 receives timing information from the neural stimulation system 106, indicating that a nerve has been stimulated. The initiated timing control 148 provides timing instructions to the event generator 150, such as a therapeutic sound generator connected by Bluetooth, such that the event generator 150 generates an event during the stimulation pulse.

Figure 25:
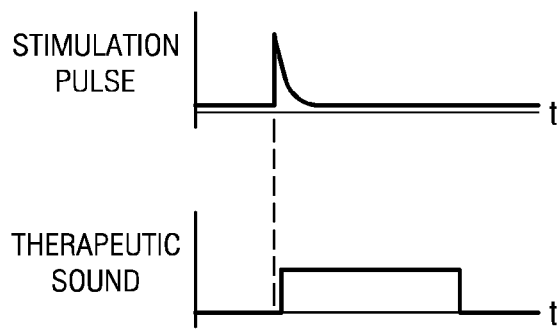
FIG. 25 is a graph depicting initiated pairing, in accordance with an embodiment.

With reference to FIG. 25, a graph shows a possible timing relationship between a neural stimulation and an event generation.

Figure 26:
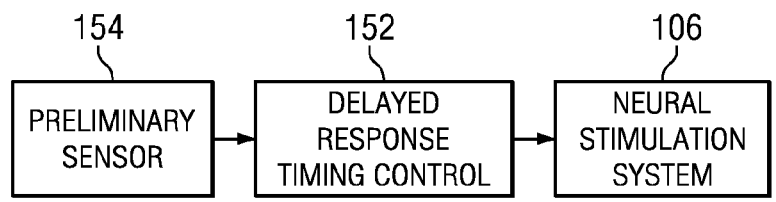
FIG. 26 is a block diagram depicting a delayed response timing control system, in accordance with an embodiment.

With reference to FIG. 26, a delayed response timing control system, in accordance with an embodiment, is shown. The delayed response timing control system includes a delayed response timing control 152. The delayed response timing control 152 is communicably connected to a neural stimulation system 106 and a preliminary event sensor 154. The preliminary event sensor 154 detects a preliminary event that anticipates a pairing event. The delayed response timing control 152 receives timing information from the preliminary event sensor 154, indicating that a preliminary event has been detected. The delayed response timing control 152 provides timing instructions to the neural stimulation system 106 to initiate nerve stimulation. In the depicted embodiment, the timing control 152 initiates the stimulation before the beginning of the pairing event, giving a negative delta t. A delay response timing system may initiate stimulation at the same time as the beginning of the pairing event, or after the beginning of the pairing event.

Figure 27:
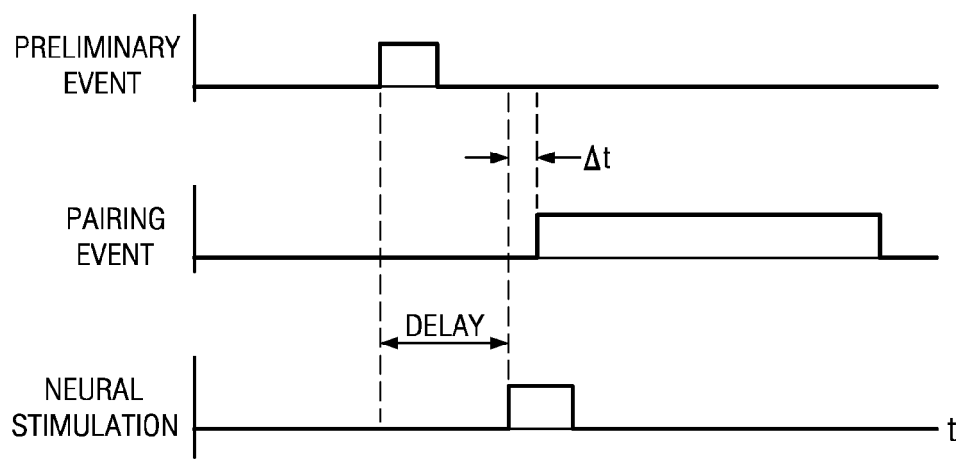
FIG. 27 is a graph depicting delayed response pairing, in accordance with an embodiment.

With reference to FIG. 27, a graph shows a possible timing relationship between a neural stimulation, a preliminary event and a pairing event.

Human and animal studies have shown that neurons deprived of auditory input begin to respond to frequencies adjacent to the region of cochlear damage. This plasticity results in a dramatic increase in the number of neurons that respond to the frequencies that order the region of hearing loss. After noise trauma, spontaneous activity in those neurons becomes highly synchronized due to abnormally high input overlaps. This synchronous activity is likely responsible for the subjective tinnitus experience. The severity of tinnitus is highly correlated (r=0.82) with cortical map reorganization caused by hearing loss. In this way, tinnitus is similar to the phantom limb pain after amputation as well as chronic pain syndromes after peripheral nerve damage. The severity of phantom limb pain in amputees is also strongly correlated (r=0.87) with the extent of map reorganization and synchronized spontaneous activity is believed to give rise to ongoing pain. Targeted neural plasticity provides a clear opportunity to restore normal operation to dysfunctional circuits.

VNS may be paired with tones to treat tinnitus. VNS may be paired with touch to treat chronic pain. VNS may be paired with skilled movement to treat motor impairments. VNS may be paired with cognitive therapy to treat cognitive impairments. VNS may be paired with desensitization therapy to treat PTSD or anxiety. VNS may be paired with speech therapy to treat communication disorders.

Figure 28:
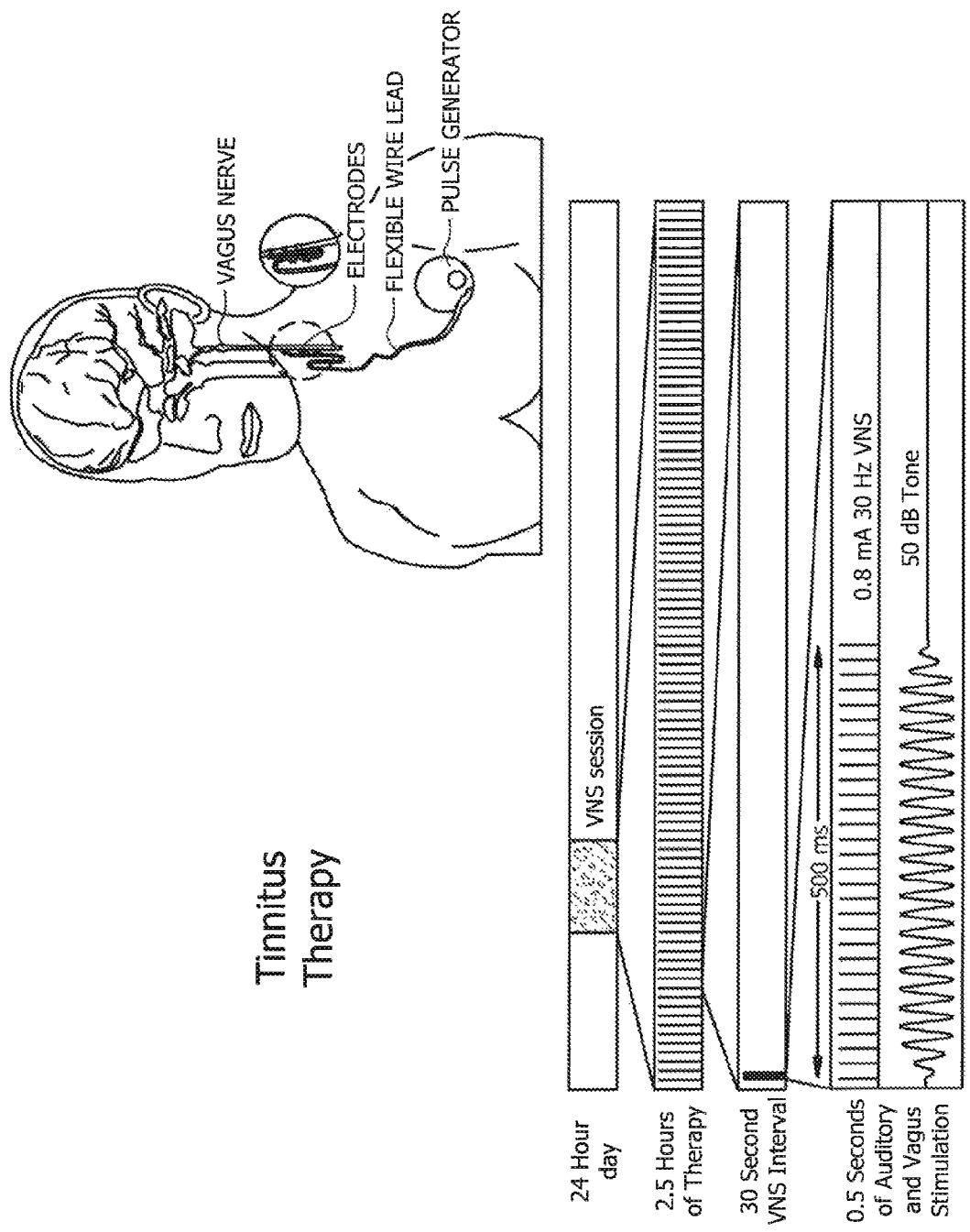
FIG. 28 depicts a tinnitus therapy, in accordance with an embodiment.

FIG. 28 depicts a tinnitus therapy, in accordance with an embodiment. A patient has a vagus nerve stimulation system implanted so that the vagus nerve electrode contacts a portion of a vagus nerve. The vagus nerve electrode is connected by a flexible wire lead to a pulse generator.

A VNS tinnitus therapy may include a 2.5-hour tinnitus therapy during a single day. During the 2.5 hour tinnitus therapy, a 50 dB tone and paired stimulation train is presented every thirty seconds, effectively presenting the pairs 300 times. Each 50 dB tone and stimulation train lasts for about 0.5 seconds. The stimulation train may be a series of 0.8 mA, 30 Hz stimulation pulses.

Figure 29:
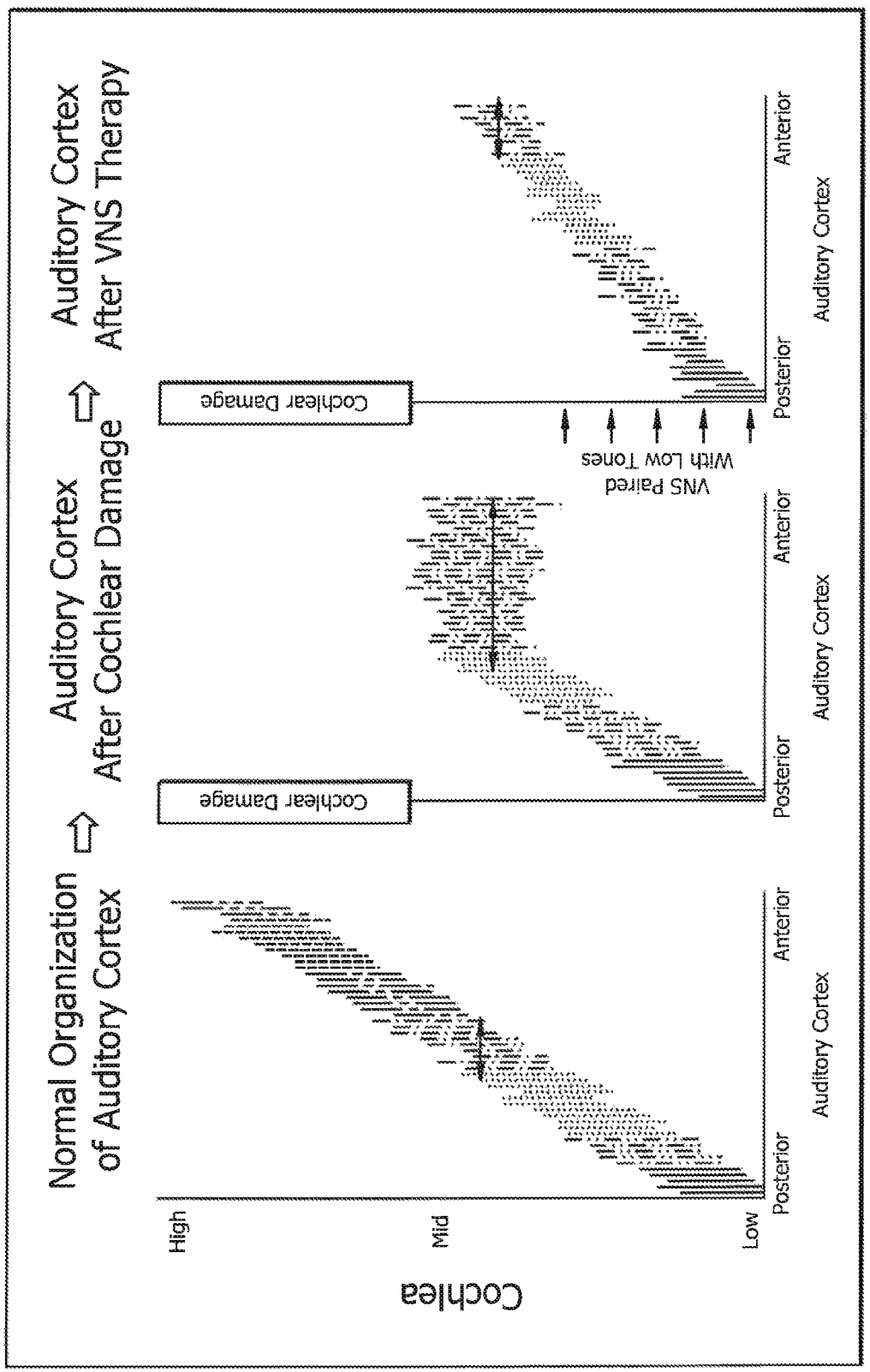
FIG. 29 depicts a schematic illustration of the proposed tinnitus pathology and treatment.

FIG. 29 depicts a schematic illustration of the tinnitus pathology and treatment. Cochlear damage at high frequencies results in map reorganization in the auditory cortex, which gives rise to the tinnitus sensation. Pairing VNS with adjacent low tones, the non-tinnitus frequencies, restores the distorted map.

As shown in FIG. 29, under normal conditions each neuron in the auditory cortex is tuned to a small range of tone frequencies (vertical lines) represented on the y-axis. Each line type represents the tone range to which the corresponding part of the auditory cortex responds. This tonotopic mapping of the auditory cortex is shown along the x-axis. The frequency preferences of auditory cortex neurons are ordered to form a topographic map from low to high in the posterior to anterior direction (FIG. 29, left). As shown in the center panel of FIG. 29, when cochlear damage was induced that removed the part of the cochlea that send signals of high frequencies to the auditory cortex, the anterior regions of the auditory cortex began to respond to the middle frequencies from the cochlea. This pathological reorganization of the auditory cortex in response to damage is accompanied by an increase in synchronous activity in the primary auditory cortex.

Vagus nerve stimulation is paired with low frequency tones to reorganize the auditory cortex as shown in the far right panel of FIG. 29. Note that neurons still do not respond to high frequencies, as those inputs have been destroyed. However, the tonotopic map of the auditory cortex has now been redistributed so that no part of the cortex exhibits the type of pathological plasticity that leads to increased synchronous activity.

The plasticity induced by neural stimulation can be paired with a variety of therapies, rehabilitation, training and other forms of personal improvement. Each therapy acts as a training source. The specific timing requirements associated with each therapy are derived from the specifics of the therapy, such that the stimulation occurs during the training, and most effectively near the beginning of the training. Some possible therapies may include behavioral therapies such as sensory discrimination for sensory deficits, motor training for motor deficits, with or without robotic assistance and cognitive training/rehabilitation for cognitive deficits. Exercise and motor therapy could be paired to treat motor deficits arising from traumatic brain injury, stroke or Alzheimer's disease and movement disorders. Constraint induced therapy could be paired to help prevent the use of alternative strategies in order to force use of impaired methods. Speech therapy could be paired for speech and language deficits. Cognitive therapies could be paired for cognitive problems.

Sensory therapies, such as tones, could be paired to treat sensory ailments such as tinnitus. In treating tinnitus, the paired tones may be at frequencies distinct from the frequencies perceived by the tinnitus patient.

Exposure or extinction therapy could be paired to treat phobias or post-traumatic stress disorder.

Computer-based therapies such as FastForward for dyslexia, Brain Fitness Program Classic or Insight, could be paired to enhance their effects. Psychotherapy could be paired, as well as other therapeutic activities in the treatment of obsessive-compulsive disorder, depression or addiction.

Biofeedback therapy could be paired. For example, temperature readings or galvanic skin responses could be paired to treat anxiety or diabetes. An electromyograph could be paired to improve motor control after brain spinal or nerve damage. A pneumograph could be paired to improve breathing control in a paralyzed patient. A real-time functional magnetic resonance image (fMRI) could be paired to improve pain control or treat obsessive-compulsive disorder (OCD). An electrodermograph, electroencephalograph (EEG), electromyograph (EMG), or electrocardiograph could be paired to treat disorders such as anxiety. An electroencephalograph could be paired to treat epilepsy. A hemoencephalography could be paired to treat migraines. A photoplethysmograph could be paired to treat anxiety. A capnometer could be paired to treat anxiety. Virtual reality therapy could be paired to treat disorders such as addiction, depression, anxiety or posttraumatic stress disorder. Virtual reality therapy could also be paired to enhance cognitive rehabilitation or performance. Drug therapies could be paired to treat a variety of conditions. Amphetamine-like compounds could be paired to enhance neuromodulators and plasticity. SSRI's could be paired to enhance neuromodulators and plasticity. MOA inhibitors could be paired to enhance neuromodulators and plasticity. Anti-coagulants could be paired to act as clot busters during acute stroke. Various drugs could be paired to stop spasm after nerve or brain damage such as Botulinum toxin, Lidocaine, etc. Small doses of drugs of abuse could be paired to extinguish cravings in addicts.

Hormone therapy could be paired. For example, progesterone, estrogen, stress, growth, or thyroid hormone, etc. could be paired to treat traumatic brain injury or Alzheimer's disease. Glucose therapy could be paired to treat anxiety. Electrical or magnetic stimulation of the central or peripheral nervous system could be paired. For example, transcranial magnetic stimulation could be used to enhance or reduce activity in a specific brain area and thereby focus the directed cortical plasticity. Transcutaneous electrical nerve stimulation could be paired to treat chronic pain, tinnitus and other disorders. Subcutaneous electrical nerve stimulation could be paired to treat chronic pain. Stem cell therapy could be paired to treat disorders such as Parkinson's disease. Gene therapy could be paired to treat conditions such as Down's syndrome, Huntington's disease or fragile X syndrome. Hyperbaric oxygen therapy could be paired to treat carbon monoxide poisoning Multiple therapies could be paired simultaneously or sequentially.

None of the description in the present application should be read as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 USC section 112 unless the exact words "means for" are followed by a participle.

The claims as filed are intended to be as comprehensive as possible, and NO subject matter is intentionally relinquished, dedicated, or abandoned.

What is claimed is:

1. A timing control system for a tinnitus therapy comprising:
   a sound generator configured to generate a plurality of sounds, wherein each sound consists of only one frequency;
   an implantable vagus nerve stimulator having an electrode and a pulse generator connected to the electrode, wherein the implantable vagus nerve stimulator is configured to stimulate a vagus nerve of a patient in contact with the electrode with an electrical pulse train from the pulse generator; and
   a control system coupled to the vagus nerve stimulator and the sound generator,
   wherein the control system is configured to receive data defining a patient's tinnitus frequencies,
   wherein the control system is configured to instruct the sound generator to generate a series of the sounds each having only one frequency,
   wherein the frequencies of the sounds are not within the patient's tinnitus frequencies and are audible to the patient,
   wherein the control system is configured to send a series of stimulation trigger signals to the implantable vagus nerve stimulator so that the pulse generator provides the electrical pulse train to the electrode and stimulates the vagus nerve with the pulse train at the same time as the generation of the sounds,
   wherein the control system is configured to cause the sound generator to generate the sounds randomly,
   wherein the control system is configured to control the intensity of the sounds, and
   wherein the control system is configured to control the duty cycle of the pulse train so that vagus nerve stimulation is followed by a period of non-stimulation at least as long as the vagus nerve stimulation.

2. The timing control system of claim 1, wherein each sound is a tone.

3. The timing control system of claim 1, wherein the pulse generator begins a pulse train before the beginning of the sounds.

4. The timing control system of claim 1, wherein the pulse generator begins a pulse train after the beginning of the sounds.

5. The timing control system of claim 1, wherein each sound is about 500 milliseconds in duration.

6. The timing control system of claim 1, wherein the pulse train is about 500milliseconds in duration.

7. The timing control system of claim 1, wherein the control system comprises a software program.

8. A timing control system for a tinnitus therapy comprising:
   a sound generator configured to generate a plurality of sounds, wherein each sound consists of only one frequency;
   an implantable vagus nerve stimulator having an electrode and a pulse generator connected to the electrode, wherein the implantable vagus nerve stimulator is configured to stimulate a vagus nerve of a patient in contact with the electrode with an electrical pulse train from the pulse generator; and
   a control system coupled to the vagus nerve stimulator and the sound generator,
   wherein the control system is configured to receive data defining a patient's tinnitus frequencies, wherein the control system is configured to instruct the sound generator to generate a series of the sounds each having only one frequency,
   wherein the frequencies of the sounds are not within the patient's tinnitus frequencies and are audible to the patient,
   wherein the control system is configured to send a series of stimulation trigger signals to the implantable vagus nerve stimulator so that the pulse generator provides the electrical pulse train to the electrode and stimulates the vagus nerve with the pulse train at the same time as the generation of the sounds.

9. The timing control system of claim 8, wherein each sound is a tone.

10. The timing control system of claim 8, wherein the pulse generator begins a pulse train before the beginning of the sounds.

11. The timing control system of claim 8, wherein the pulse generator begins a pulse train after the beginning of the sounds.

12. The timing control system of claim 8, wherein each sound is about 500 milliseconds in duration.

13. The timing control system of claim 8, wherein the pulse train is about 500 milliseconds in duration.

14. The timing control system of claim 8, wherein the control system is a software program.

15. The timing control system of claim 8, wherein the sounds are generated randomly.

16. The timing control system of claim 8, wherein the control system is configured to cause the sound generator to repeat the sounds.

17. The timing control system of claim 8, wherein the control system is configured to control the intensity of the sounds.

18. The timing control system of claim 8, wherein the control system is configured to control the duty cycle of the pulse train so that vagus nerve stimulation is followed by a period of non-stimulation at least as long as the vagus nerve stimulation.

* * * * *